(12) United States Patent
Gurevich

(10) Patent No.: US 10,636,144 B2
(45) Date of Patent: Apr. 28, 2020

(54) METHODS AND SYSTEMS FOR ASSESSING HEALING OF TISSUE

(71) Applicant: Novadaq Technologies ULC, Burnaby (CA)

(72) Inventor: Lina Gurevich, Vancouver (CA)

(73) Assignee: Novadaq Technologies ULC, Burnaby (CA)

(*) Notice: Subject to any disclaimer, the term of this patent is extended or adjusted under 35 U.S.C. 154(b) by 0 days.

(21) Appl. No.: 16/430,022

(22) Filed: Jun. 3, 2019

(65) Prior Publication Data

US 2019/0355116 A1 Nov. 21, 2019

Related U.S. Application Data

(63) Continuation of application No. 15/224,088, filed on Jul. 29, 2016, now Pat. No. 10,311,567.

(Continued)

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0071* (2013.01); *A61B 5/0261* (2013.01);
(Continued)

(58) Field of Classification Search
CPC ......... G06T 7/0012; G06T 2207/10064; G06T 2207/30088
See application file for complete search history.

(56) References Cited

U.S. PATENT DOCUMENTS

| 6,577,884 B1 | 6/2003 | Boas |
| 7,474,906 B2 | 1/2009 | Rubinstein et al. |

(Continued)

FOREIGN PATENT DOCUMENTS

| JP | 2003-510121 A | 3/2003 |
| JP | 2008-532682 A | 8/2008 |

(Continued)

OTHER PUBLICATIONS

Alm, A. et al. (1973). "Ocular and Optic Nerve Blood Flow at Normal and Increased Intraocular Pressures in Monkeys (*Macaca irus*): A Study with Radioactively Labelled Microspheres including Flow Determinations in Brain and Some Other Tissues," Experimental Eye Research 15:15-29.

(Continued)

*Primary Examiner* — Kim Y Vu
*Assistant Examiner* — Molly Delaney
(74) *Attorney, Agent, or Firm* — Morrison & Foerster LLP

(57) ABSTRACT

A method for assessing healing of a subject includes receiving a time series of signal intensity data capturing the transit of an imaging agent through tissue over a period of time, wherein the tissue comprises a plurality of calculation regions and wherein signal intensity in each calculation region over the period of time may be approximated by a time-intensity curve corresponding to the calculation region; determining, for each calculation region, a coefficient value that is related to at least a portion of the time-intensity curve corresponding to the calculation region; and converting the coefficient values across the plurality of calculation regions into a coefficient-derived image map.

17 Claims, 26 Drawing Sheets
(19 of 26 Drawing Sheet(s) Filed in Color)

Related U.S. Application Data

(60) Provisional application No. 62/222,630, filed on Sep. 23, 2015.

(51) Int. Cl.
    *A61B 5/026*         (2006.01)
    *A61B 5/0275*      (2006.01)

(52) U.S. Cl.
    CPC ............ *A61B 5/0275* (2013.01); *A61B 5/445* (2013.01); *A61B 5/4842* (2013.01); *A61B 5/4848* (2013.01); *A61B 5/7239* (2013.01); *A61B 5/7275* (2013.01); *A61B 2576/02* (2013.01); *G06T 2207/10064* (2013.01); *G06T 2207/30088* (2013.01)

(56) References Cited

U.S. PATENT DOCUMENTS

| | | | |
|---|---|---|---|
| 8,285,353 | B2 | 10/2012 | Choi et al. |
| 8,718,747 | B2 | 5/2014 | Bjørnerud et al. |
| 9,451,903 | B2* | 9/2016 | Feinberg ................ A61B 5/055 |
| 10,285,603 | B2 | 5/2019 | Flower |
| 10,311,567 | B2 | 6/2019 | Gurevich |
| 2002/0007123 | A1* | 1/2002 | Balas ..................... A61B 1/303 600/476 |
| 2003/0127609 | A1 | 7/2003 | El Hage et al. |
| 2005/0065432 | A1* | 3/2005 | Kimura ................ A61B 5/0263 600/420 |
| 2006/0011853 | A1* | 1/2006 | Spartiotis .......... H01L 27/14634 250/370.13 |
| 2008/0188728 | A1 | 8/2008 | Neumann et al. |
| 2008/0221421 | A1 | 9/2008 | Choi et al. |
| 2009/0112097 | A1* | 4/2009 | Kato ....................... A61B 8/461 600/458 |
| 2010/0061604 | A1 | 3/2010 | Nahm et al. |
| 2010/0080757 | A1* | 4/2010 | Haaga .................. A61B 5/0263 424/9.3 |
| 2012/0323118 | A1 | 12/2012 | Menon Gopalakrishna et al. |
| 2014/0163403 | A1* | 6/2014 | Lenox .................... A61B 5/026 600/504 |
| 2014/0254909 | A1* | 9/2014 | Carmi .................... A61B 6/032 382/131 |
| 2014/0371583 | A1 | 12/2014 | Flower |
| 2015/0112192 | A1 | 4/2015 | Docherty et al. |
| 2015/0164396 | A1 | 6/2015 | Acharya et al. |
| 2015/0182137 | A1 | 7/2015 | Flower et al. |
| 2015/0248758 | A1* | 9/2015 | Pautot ........................ G06T 7/20 382/131 |
| 2016/0253800 | A1 | 9/2016 | Gurevich et al. |
| 2017/0084024 | A1 | 3/2017 | Gurevich |
| 2017/0245766 | A1 | 8/2017 | Flower et al. |

FOREIGN PATENT DOCUMENTS

| | | |
|---|---|---|
| JP | 2008-220926 A2 | 9/2008 |
| JP | 2010-505582 A | 2/2010 |
| JP | 2013-502263 A | 1/2013 |
| WO | WO-90/12537 A1 | 11/1990 |
| WO | WO-2009/127972 A2 | 10/2009 |
| WO | WO-2015/001427 A2 | 1/2015 |

OTHER PUBLICATIONS

Australian Notice of Acceptance dated Jun. 12, 2019 for Australian Patent Application No. 2016325592 filed on Mar. 21, 2018, three pages.
Australian Office Action dated Jun. 28, 2018 for Australian Patent Application No. 2016325592 filed on Mar. 21, 2018, four pages.
Canadian Office Action dated Aug. 14, 2018 for Canadian Patent application No. 2,913,692 filed on Nov. 26, 2015, three pages.
Canadian Office Action dated Aug. 28, 2017 for Canadian Patent application No. 2,913,692 filed on Nov. 26, 2015, three pages.
Canadian Office Action dated Feb. 28, 2019 for Canadian Patent application No. 2,998,699 filed on Mar. 14, 2018, nine pages.
Canadian Office Action dated Jul. 11, 2019, for Patent Application No. 2913692, filed on Nov. 26, 2015, three pages.
Canadian Office Action dated Nov. 4, 2016 for Canadian Patent application No. 2,913,692 filed on Nov. 26, 2015, five pages.
Chinese Office Action dated May 23, 2019 for Chinese Application No. 201480044769.1 filed on Jun. 16, 2014, twelve pages. (includes English translation).
Chinese Office Action dated Sep. 25, 2019 for Chinese Application No. 201480044769.1 filed on Jun. 16, 2014, ten pages. (includes English translation).
Elgendi, M. (Feb. 2012). "On the Analysis of Fingertip Photoplethysmogram Signals," Current Cardiology Reviews 8(1):14-25.
Eren, S. et al. (Dec. 1995). "Assessment of Microcirculation of an Axial Skin Flap Using Indocyanine Green Fluorescence Angiography," Plastic and Reconstructive Surgery 96(7):1636-1649.
European Communication Pursuant to Rules 70(2) and 70a(2) EPC dated May 23, 2017 for EP Application No. 14820367.2, filed on Nov. 25, 2015, one page.
European Extended Search Report dated May 4, 2017 for EP Application No. 14820367.2, filed on Nov. 25, 2015, ten pages.
European Communication Under Rule 71(3) EPC, Intention to Grant, dated Mar. 19, 2019 for EP Application No. 14820367.2, filed on Nov. 25, 2015, six pages.
European Office Action dated May 18, 2018 for EP Application No. 14820367.2, filed on Nov. 25, 2015, five pages.
European Supplementary Partial Search Report dated Jan. 20, 2017 for EP Application No. 14820367.2, filed on Nov. 25, 2015, seven pages.
Flower, R.W. (Dec. 1973). "Injection Technique for Indocyanine Green and Sodium Fluorescein Dye Angiography of the Eye," Investigative Ophthalmology 12:881-895.
Flower, R.W. et al. (Aug. 1977). "Quantification of Indicator Dye Concentration in Ocular Blood Vessels," Exp. Eye Res. 25(2):103-111.
Humphreys, K. et al. (2007; e-published Apr. 23, 2007). "Noncontract Simultaneous Dual Wavelength Photoplethysmogrphy: A Further Step Toward Noncontract Pulse Oximetry," Review of Scientific Instruments 78:044304, six pages.
International Preliminary Report on Patentability dated Apr. 5, 2018 for International Application No. PCT/IB2016/001216 filed on Jul. 29, 2016, six pages.
International Preliminary Report on Patentability dated Aug. 30, 2018 for International Application No. PCT/CA2017/050189 filed on Feb. 15, 2017, seven pages.
International Search Report and Written Opinion dated Dec. 28, 2016 for International Application No. PCT/IB2016/001216 filed on Jul. 29, 2016, eight pages.
International Search Report and Written Opinion dated Feb. 5, 2015 for International Application No. PCT/IB014/002184 filed on Jun. 16, 2014, eleven pages.
International Search Report and Written Opinion dated May 11, 2017, for International Application No. PCT/CA2017/050189, filed on Feb. 15, 2017, eleven pages.
Japanese Notice of Allowance dated Feb. 16, 2018 for Japanese Patent Application No. 2016-518598 filed on Dec. 9, 2015, six pages. (includes English translation).
Japanese Office Action dated Jul. 1, 2019, for Patent Application No. 2018-515609, filed on Jul. 29, 2016, nine pages. (includes English translation).
Japanese Office Action dated Nov. 14, 2016 for Japanese Patent Application No. 2016-518598 filed on Dec. 9, 2015, five pages. (includes English translation).
Japanese Office Action dated Jun. 30, 2017 for JP Application No. 2016-518598, filed on Dec. 9, 2015, four pages. (includes English translation).
Jayanthy, A.K. et al. (Feb. 2011). "Measuring Blood Flow: Techniques and Applications—A Review," IJRRAS 6(2):203-216.
Korean Office Action dated Jan. 8, 2020, for Korean Patent Application No. 10-2019-7033703, filed Jun. 16, 2014, 5 pages. (includes English translation).

(56) References Cited

OTHER PUBLICATIONS

Korean Office Action dated Jan. 28, 2019 for KR Application No. 10-2016-7000943 filed on Jan. 13, 2016, five pages. (includes English translation).
Korean Office Action dated Jun. 27, 2018 for KR Application No. 10-2016-7000943 filed on Jan. 13, 2016, four pages. (includes English translation).
Korean Office Action dated May 13, 2019 for KR Application No. 10-2016-7000943 filed on Jan. 13, 2016, eight pages. (includes English translation).
Korean Office Action dated Oct. 19, 2017 for KR Application No. 10-2016-7000943 filed on Jan. 13, 2016, ten pages. (includes English translation).
Maarek, J.I. et al. (Mar. 1, 2007). "Fluorescence Dilution Technique for Measurement of Cardiac Output and Circulating Blood Volume in Healthy Human Subjects," Anesthesiology 106(3):491-498.
Mitra, S. et al. (Sep. 1, 2003). "Serial Determinations of Absolute Plasma Volume with Indocyanine Green During Hemodialysis," Journal of American Society of Nephrology (JASN) 14:2345-2351.
Nadler, S.B. et al. (Feb. 1962). "Prediction of Blood Volume In Normal Human Adults," Surgery 51(2):224-232.
Nunan, R. et al. (2014). "Clinical Challenges of Chronic Wounds: Searching for an Optimal Animal Model to Recapitulate their Complexity," The Company of Biologists—Disease Models & Mechanisms 7:1205-1213.
Stadler, I. et al. (Jul.-Aug. 2004). "Development of a simple, noninvasive, clinically relevant model of pressure ulcers in the mouse," Journal of Investigative Surgery 17(4):221-227.

U.S. Final Office Action dated Apr. 12, 2019, for U.S. Appl. No. 15/433,502, filed Feb. 15, 2017, seven pages.
U.S. Final Office Action dated Jul. 14, 2017, for U.S. Appl. No. 14/305,950, filed Jun. 16, 2014, thirteen pages.
U.S. Final Office Action dated Jul. 20, 2018, for U.S. Appl. No. 15/224,088, filed Jul. 29, 2016, seven pages.
U.S. Final Office Action dated Jun. 22, 2017, for U.S. Appl. No. 14/510,848, filed Oct. 9, 2014, fourteen pages.
U.S. Non Final Office Action dated Feb. 23, 2018, for U.S. Appl. No. 15/224,088, filed Jul. 29, 2016, nineteen pages.
U.S. Non Final Office Action dated Jun. 28, 2018, for U.S. Appl. No. 14/510,848, filed Oct. 9, 2014, eighteen pages.
U.S. Non Final Office Action dated Sep. 17, 2018, for U.S. Appl. No. 15/433,502, filed Feb. 15, 2017, eleven pages.
U.S. Non Final Office Action dated Sep. 22, 2016, for U.S. Appl. No. 14/305,950, filed Jun. 16, 2014, nine pages.
U.S. Non Final Office Action dated Sep. 28, 2016, for U.S. Appl. No. 14/510,848, filed Oct. 9, 2014, twenty pages.
U.S. Notice of Allowance dated Dec. 16, 2019, for U.S. Appl. No. 15/433,502, filed Feb. 15, 2017, seven pages.
U.S. Notice of Allowance dated Aug. 28, 2019, for U.S. Appl. No. 15/433,502, filed Feb. 15, 2017, eight pages.
U.S. Notice of Allowance dated Dec. 12, 2018, for U.S. Appl. No. 15/224,088, filed Jul. 29, 2016, nine pages.
U.S. Notice of Allowance dated Dec. 28, 2018, for U.S. Appl. No. 14/305,950, filed Jun. 16, 2014, ten pages.
U.S. Notice of Allowance dated Mar. 27, 2019, for U.S. Appl. No. 14/510,848, filed Oct. 9. 2014, ten pages.

* cited by examiner 510    520a 510    520b 510    520c 510    520d

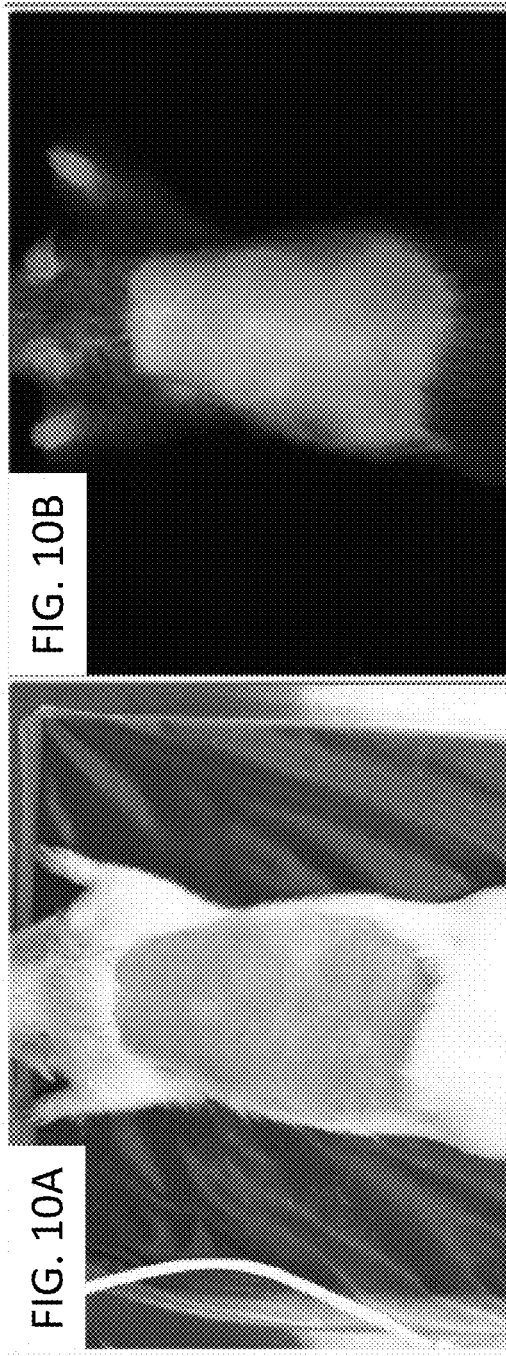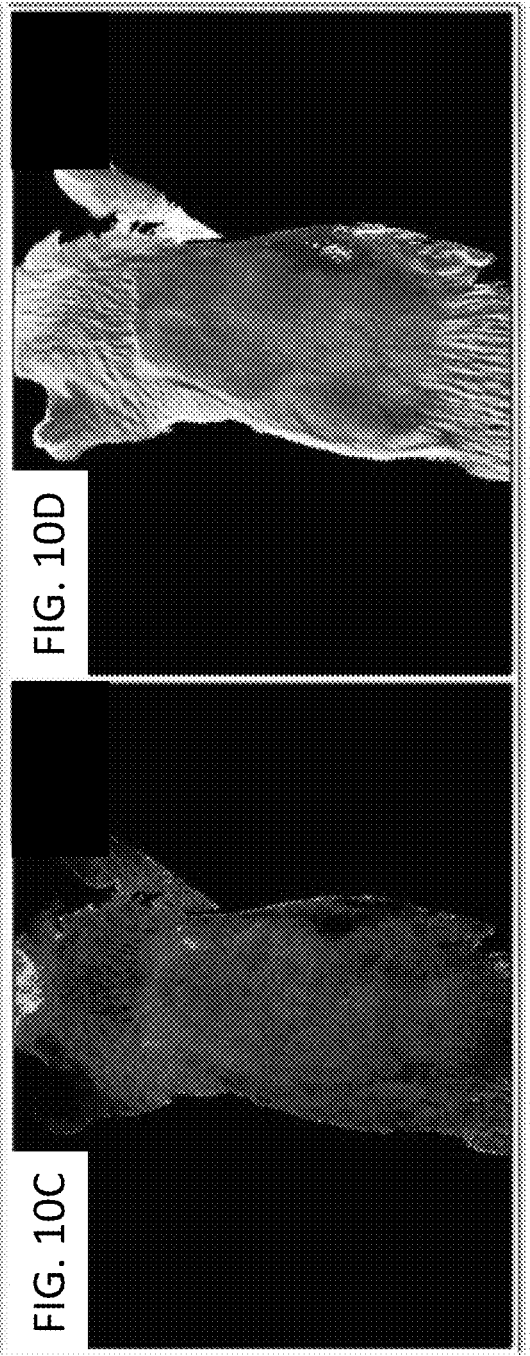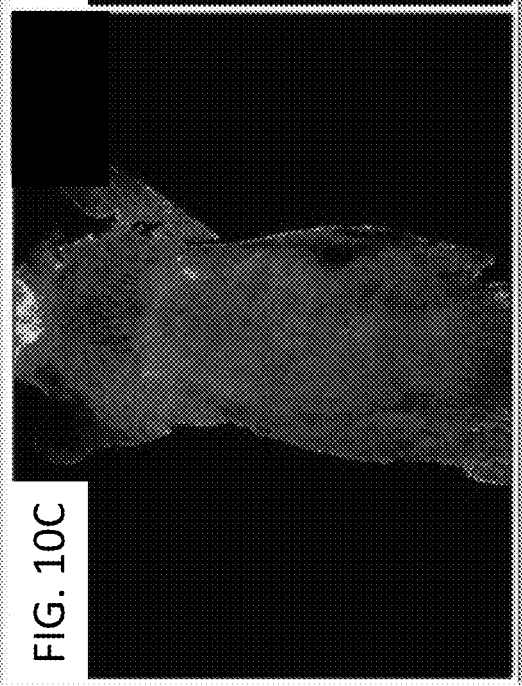

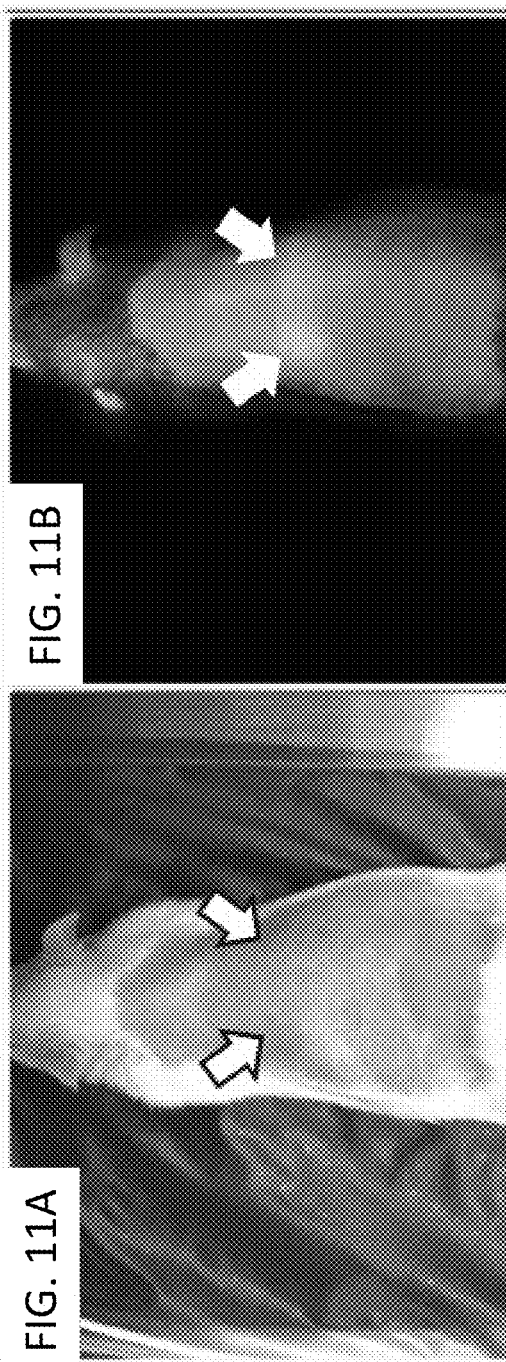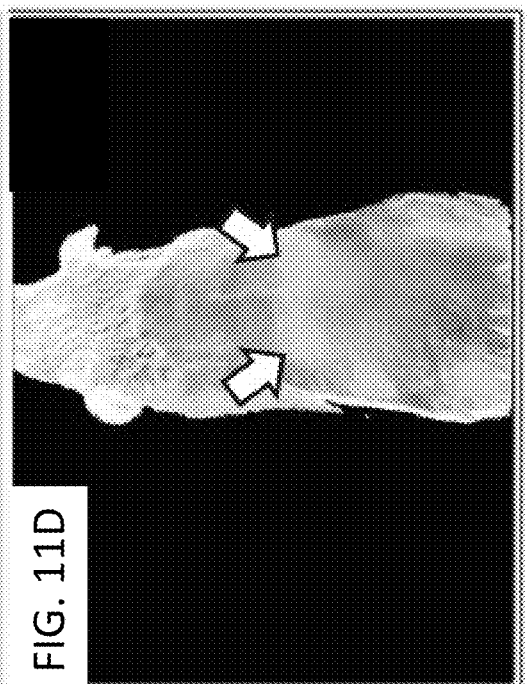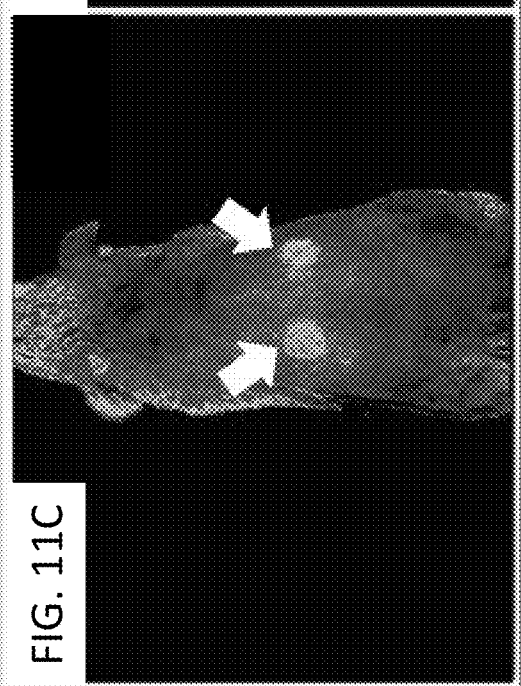

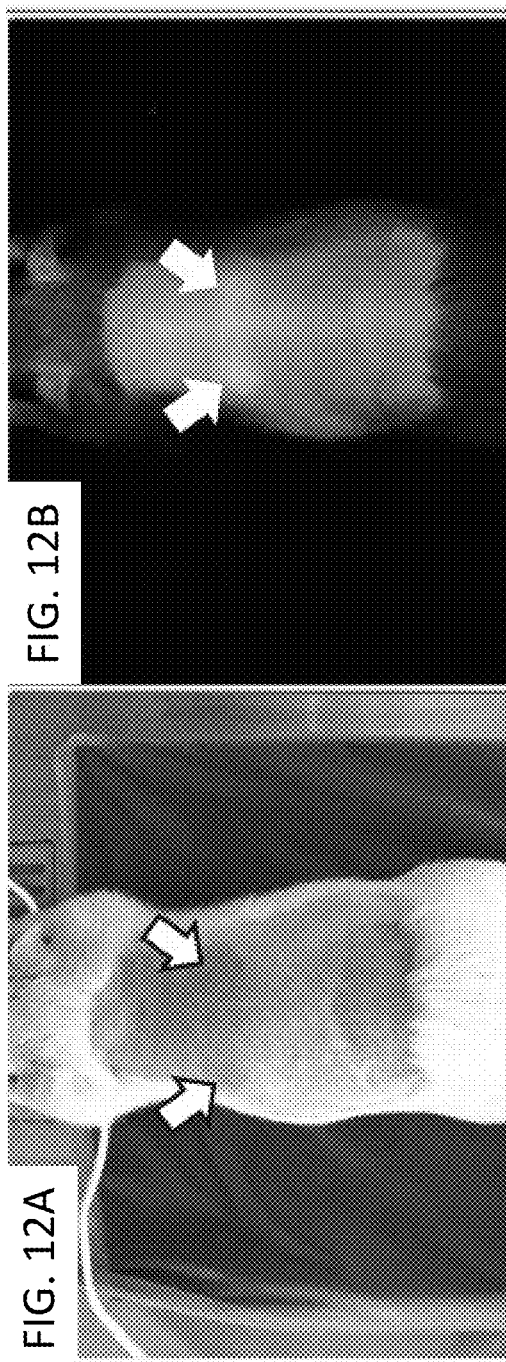
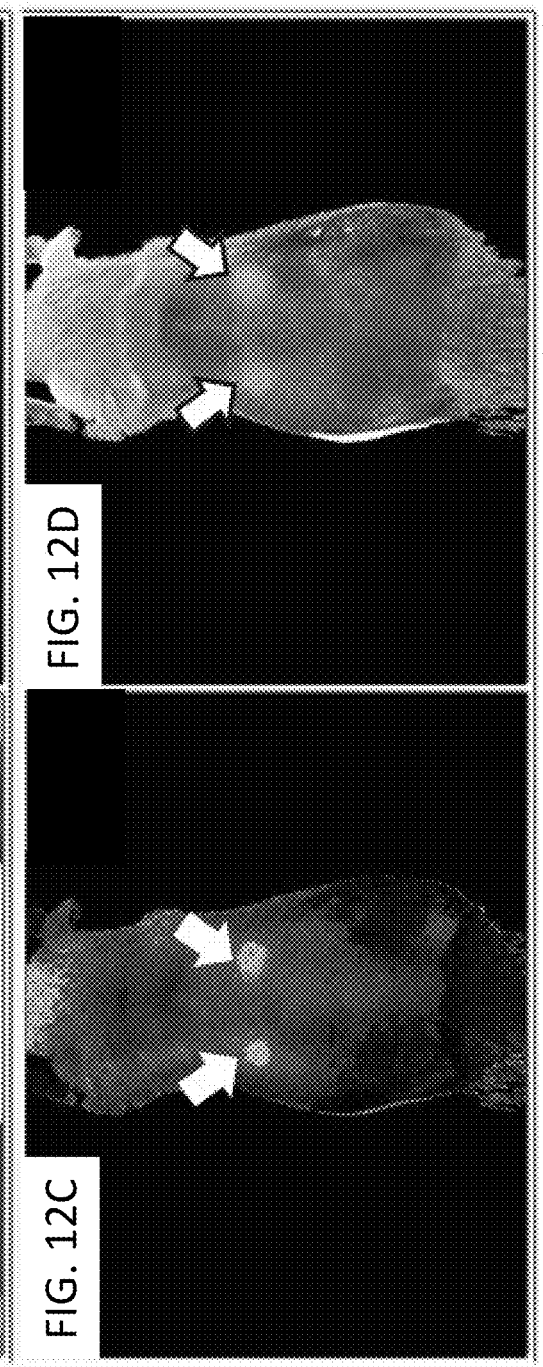
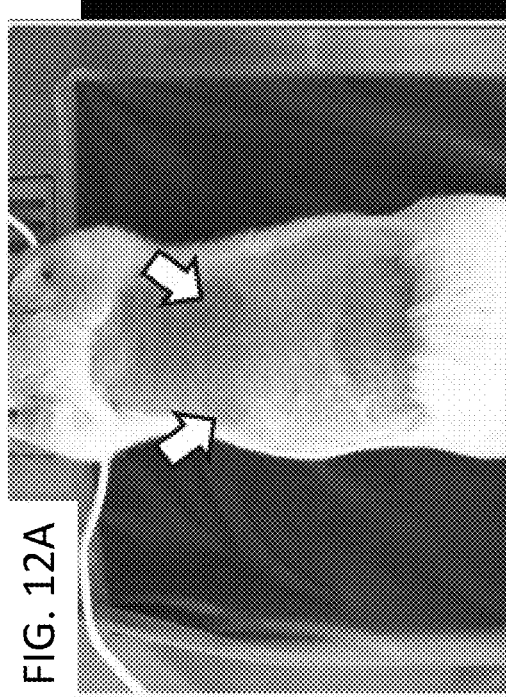
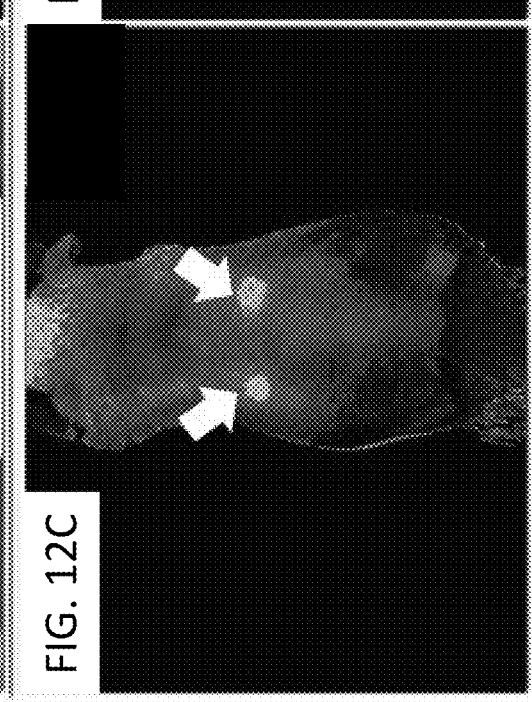

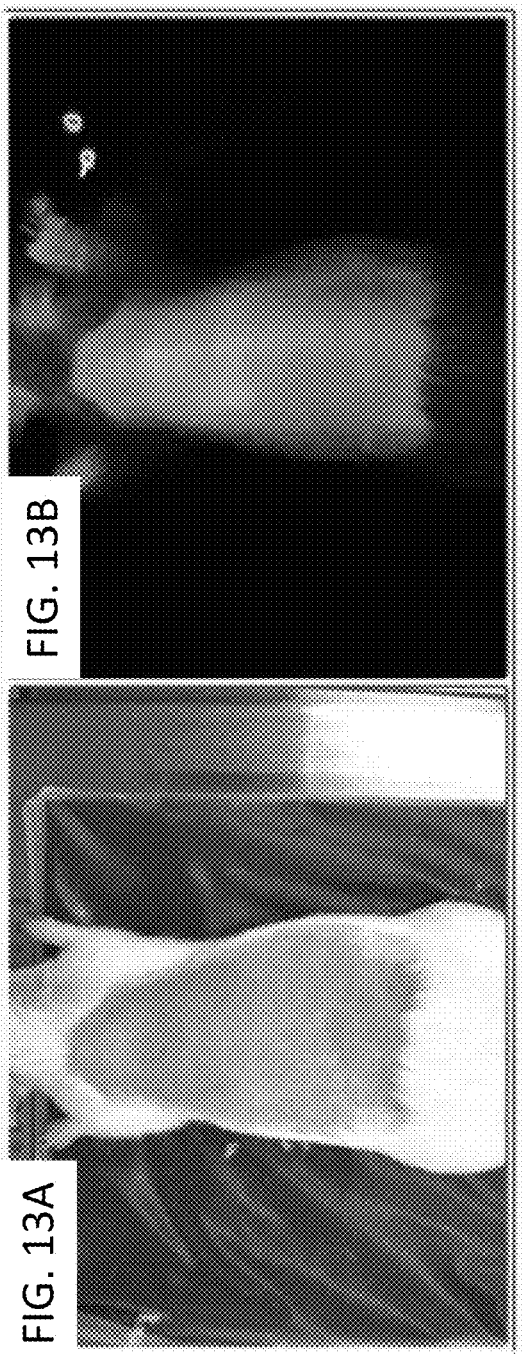
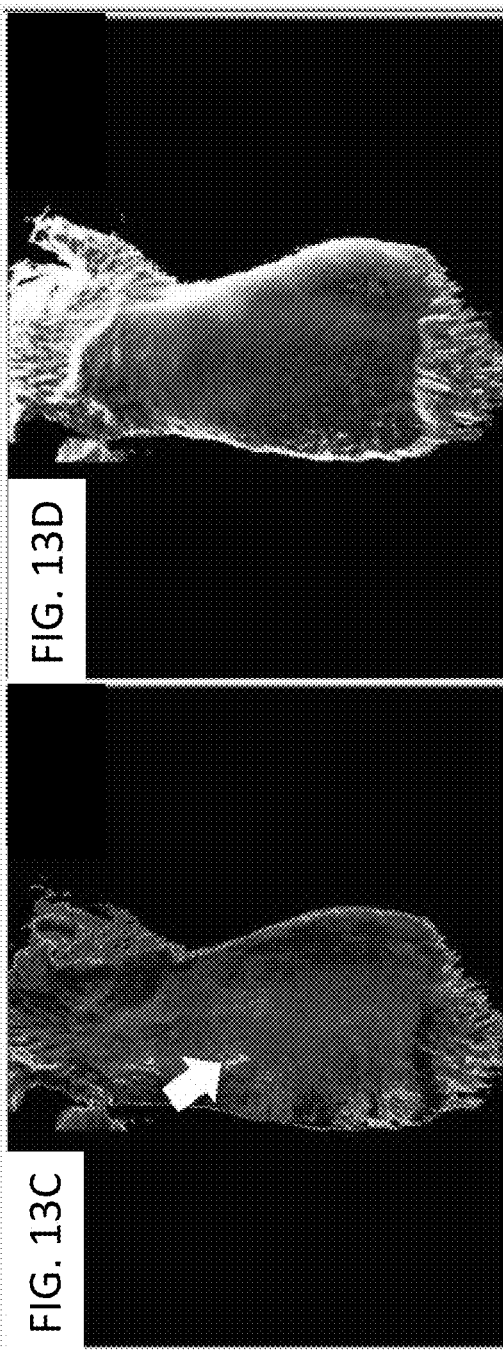
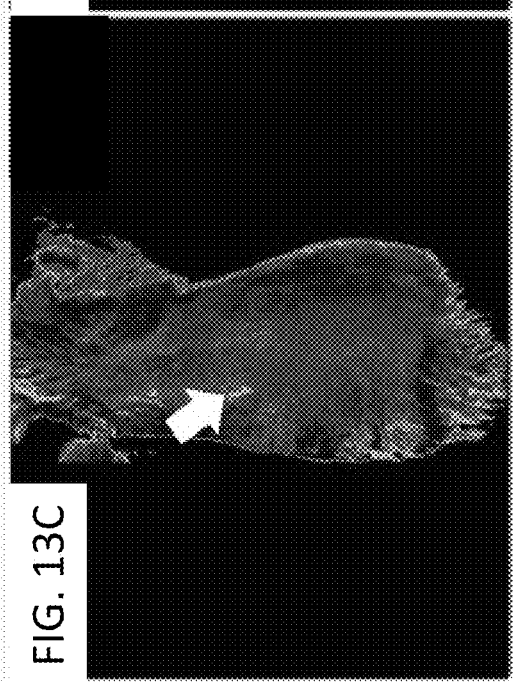
FIG. 13A
FIG. 13B
FIG. 13C
FIG. 13D

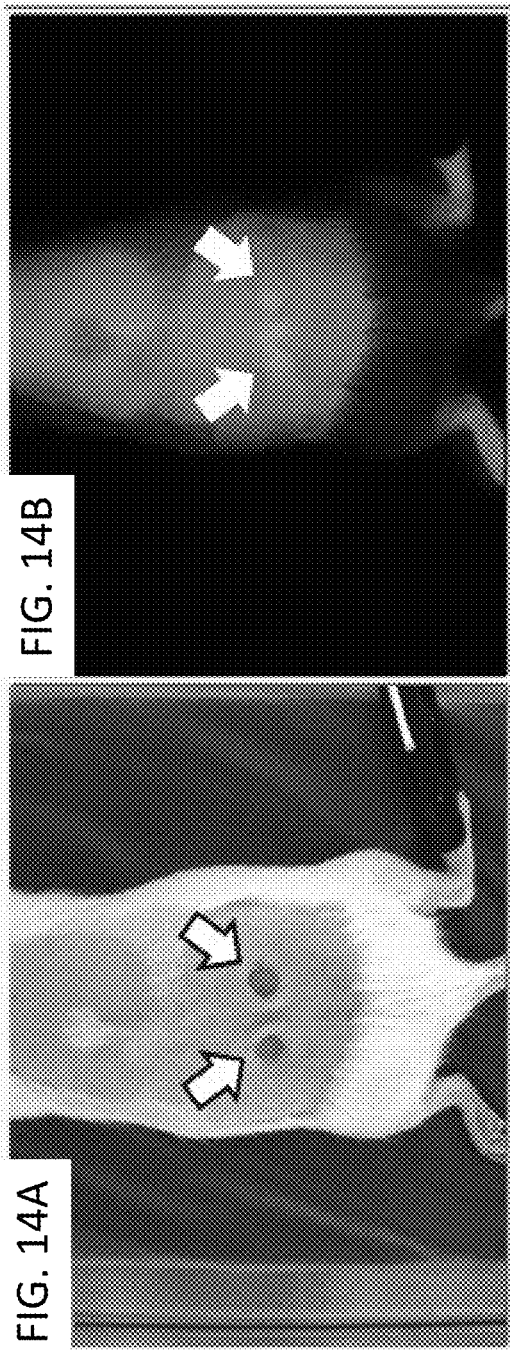
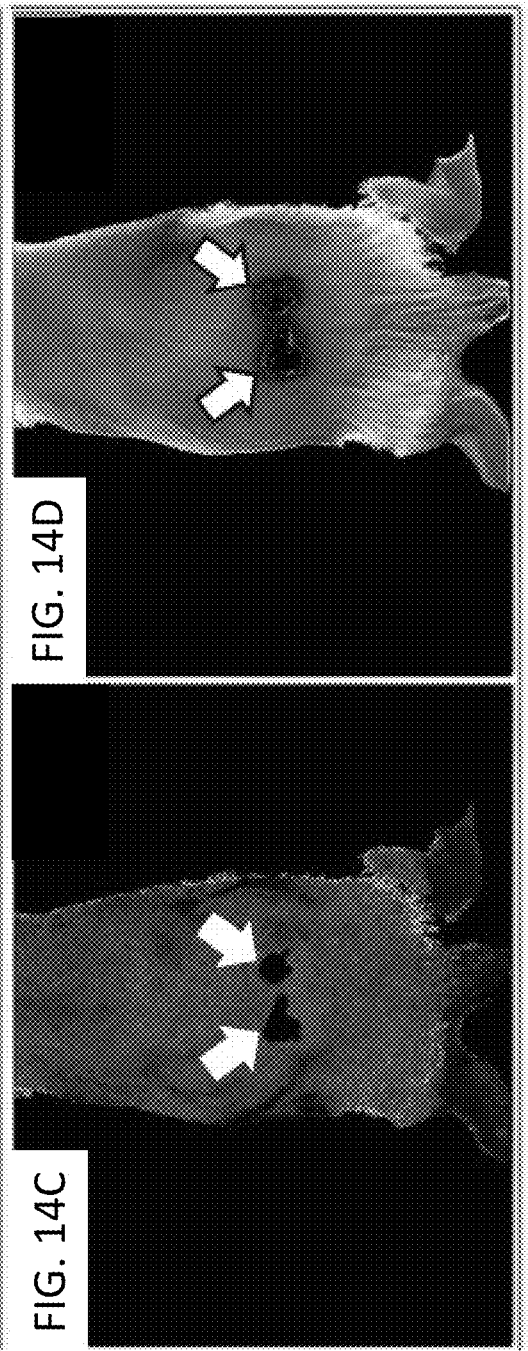
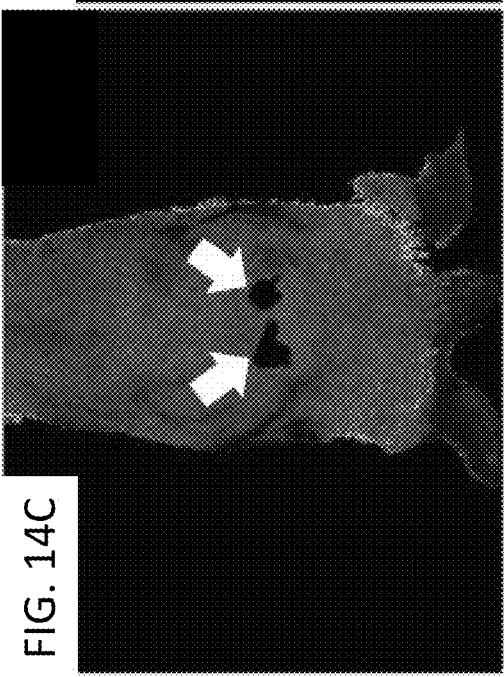

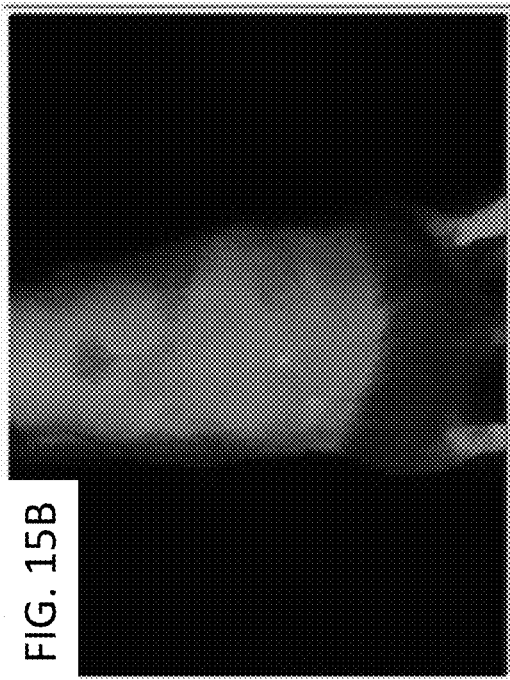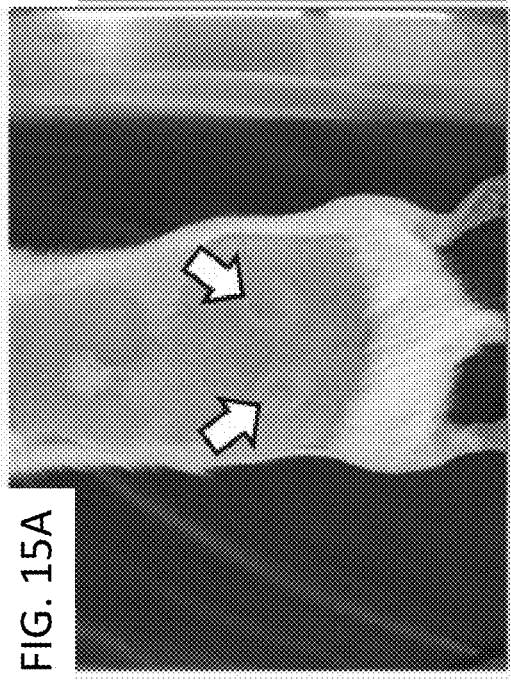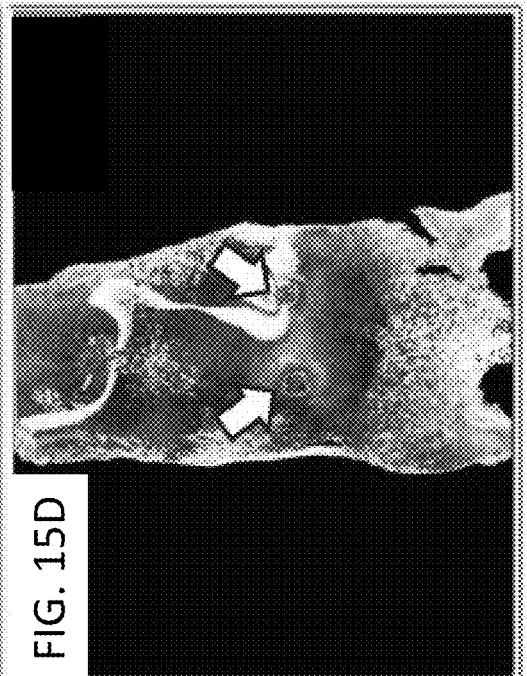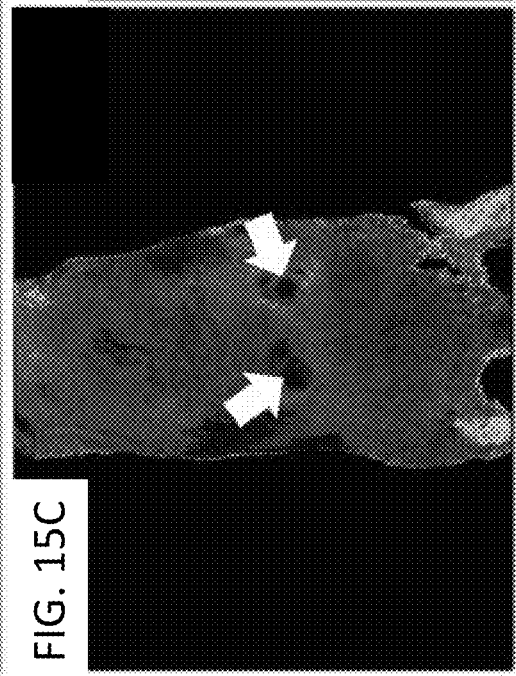

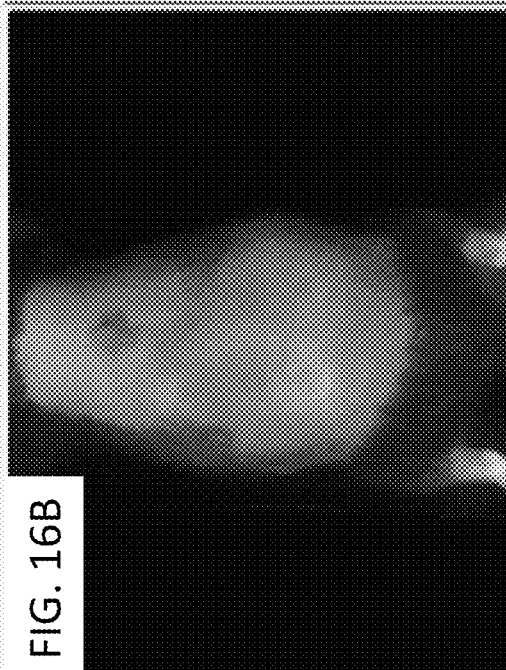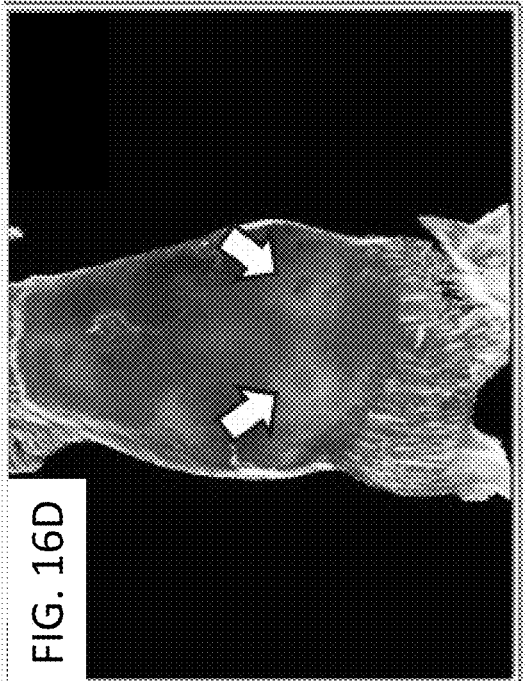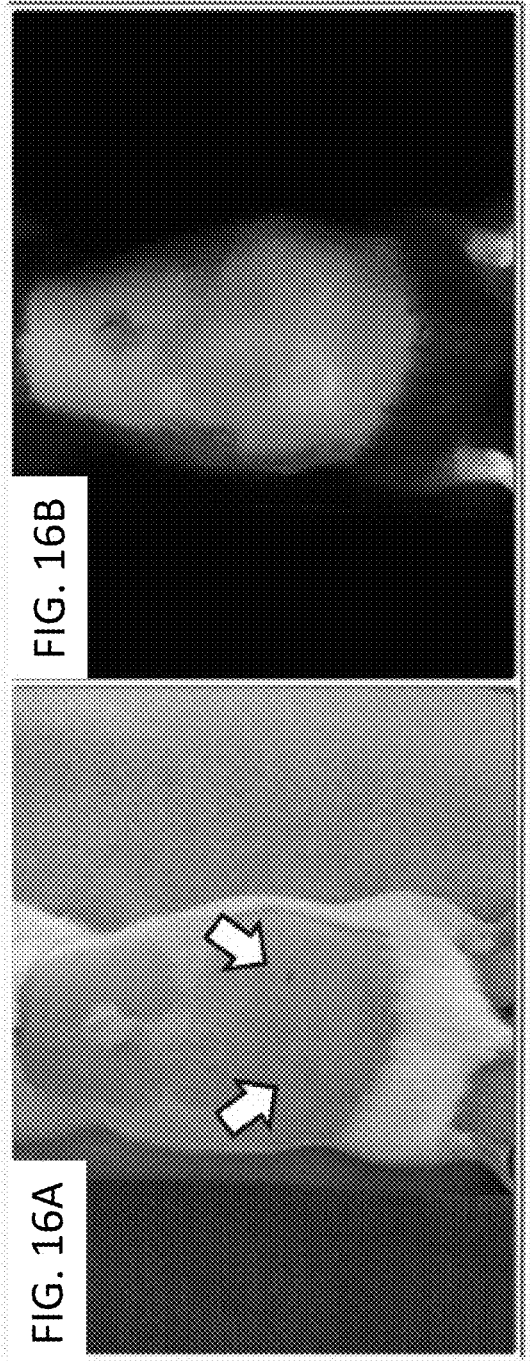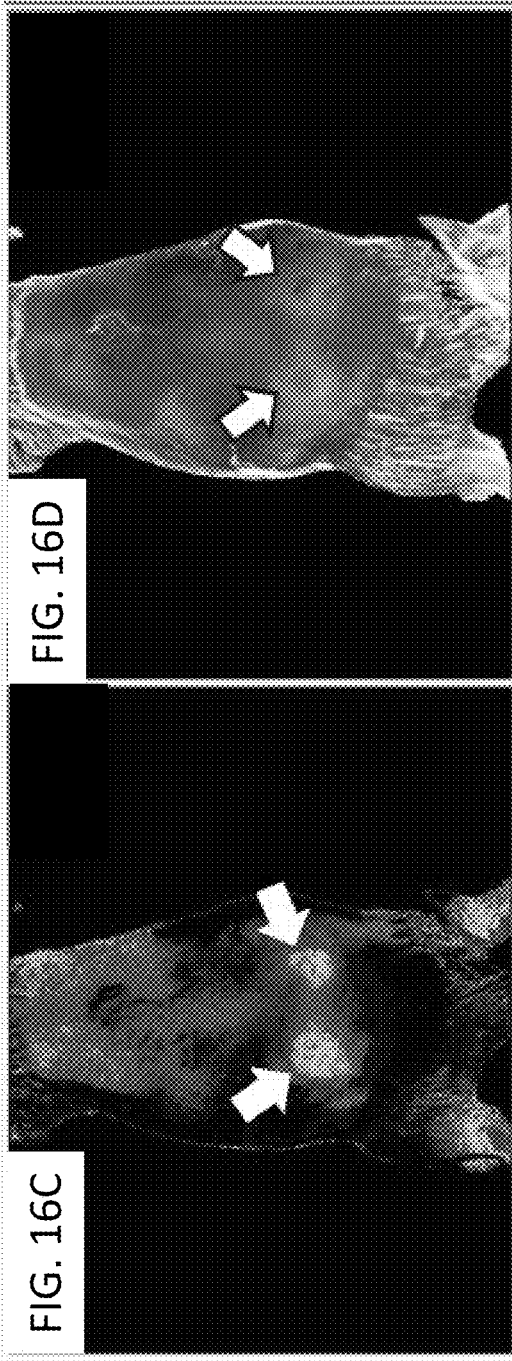

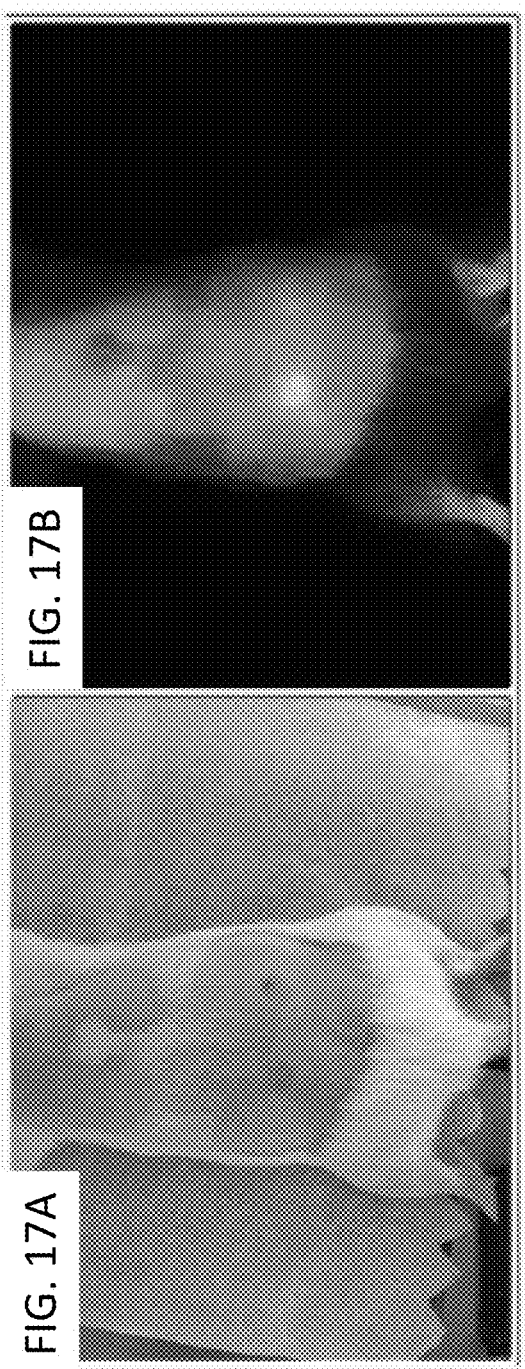

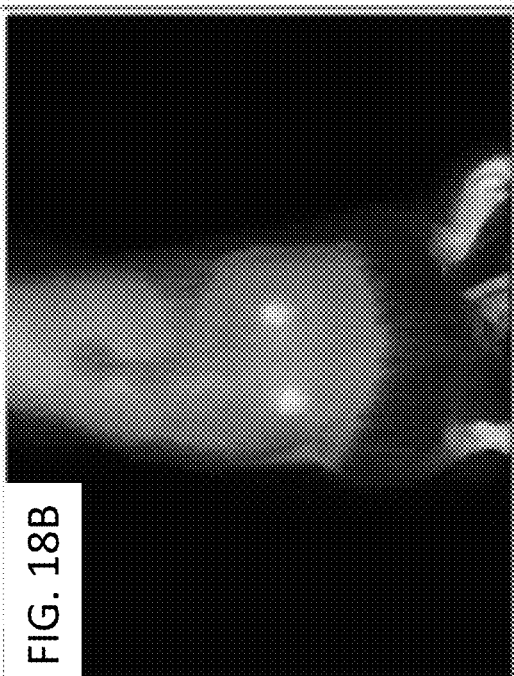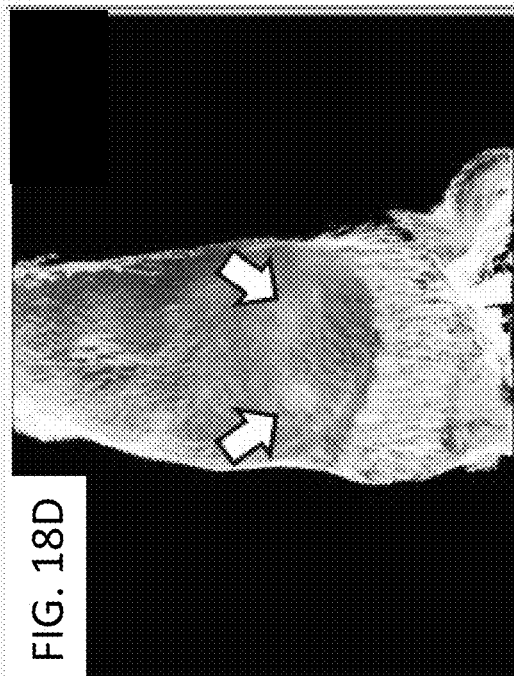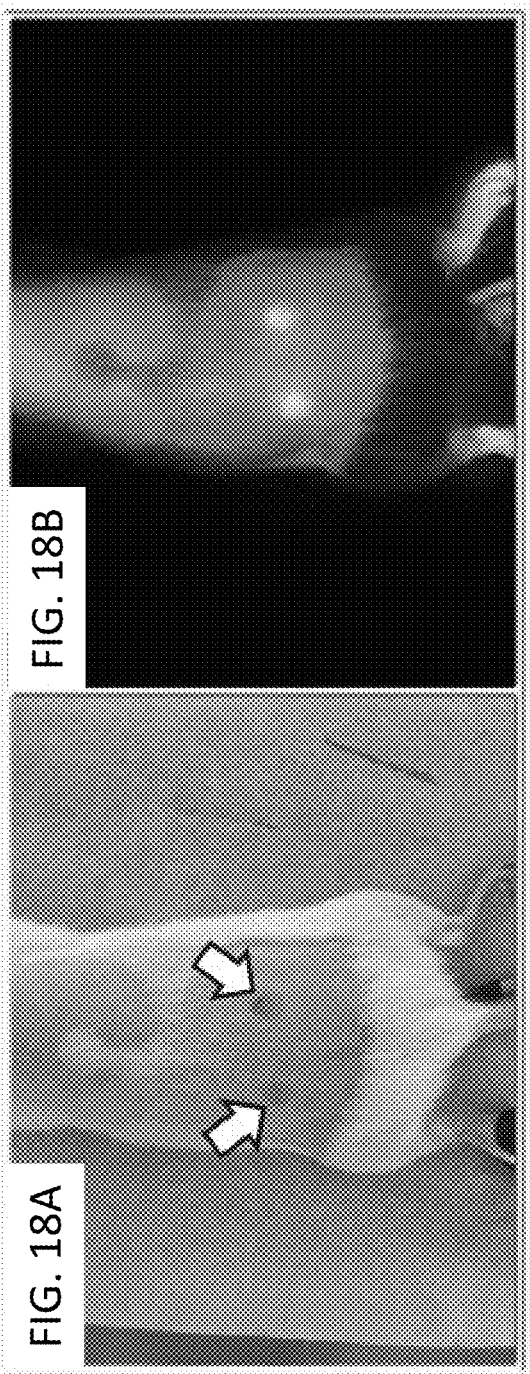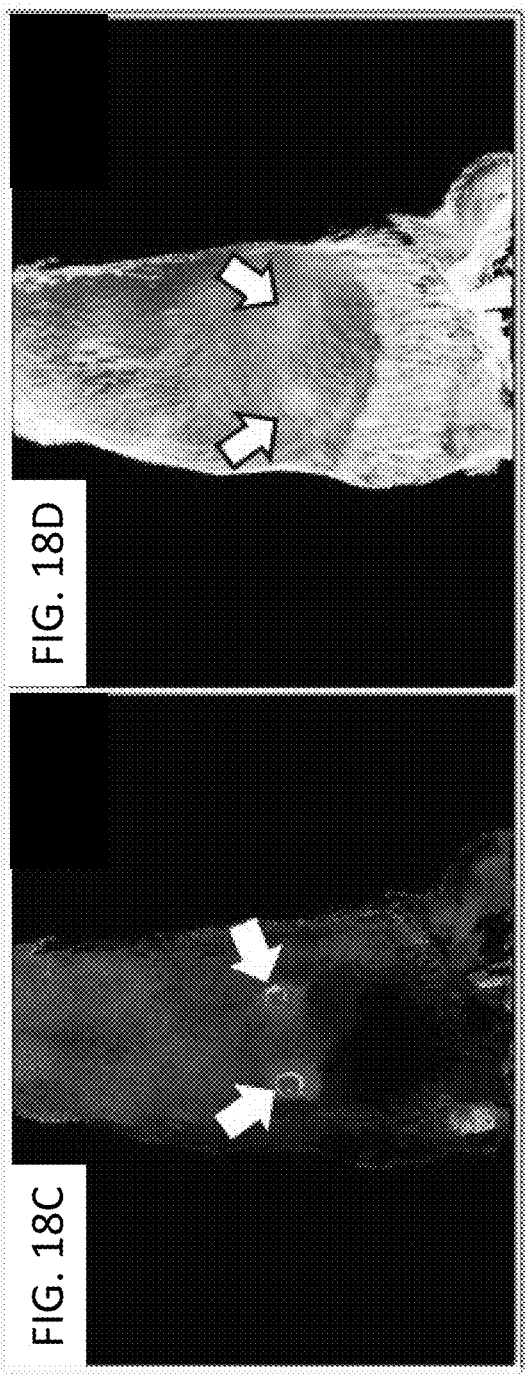

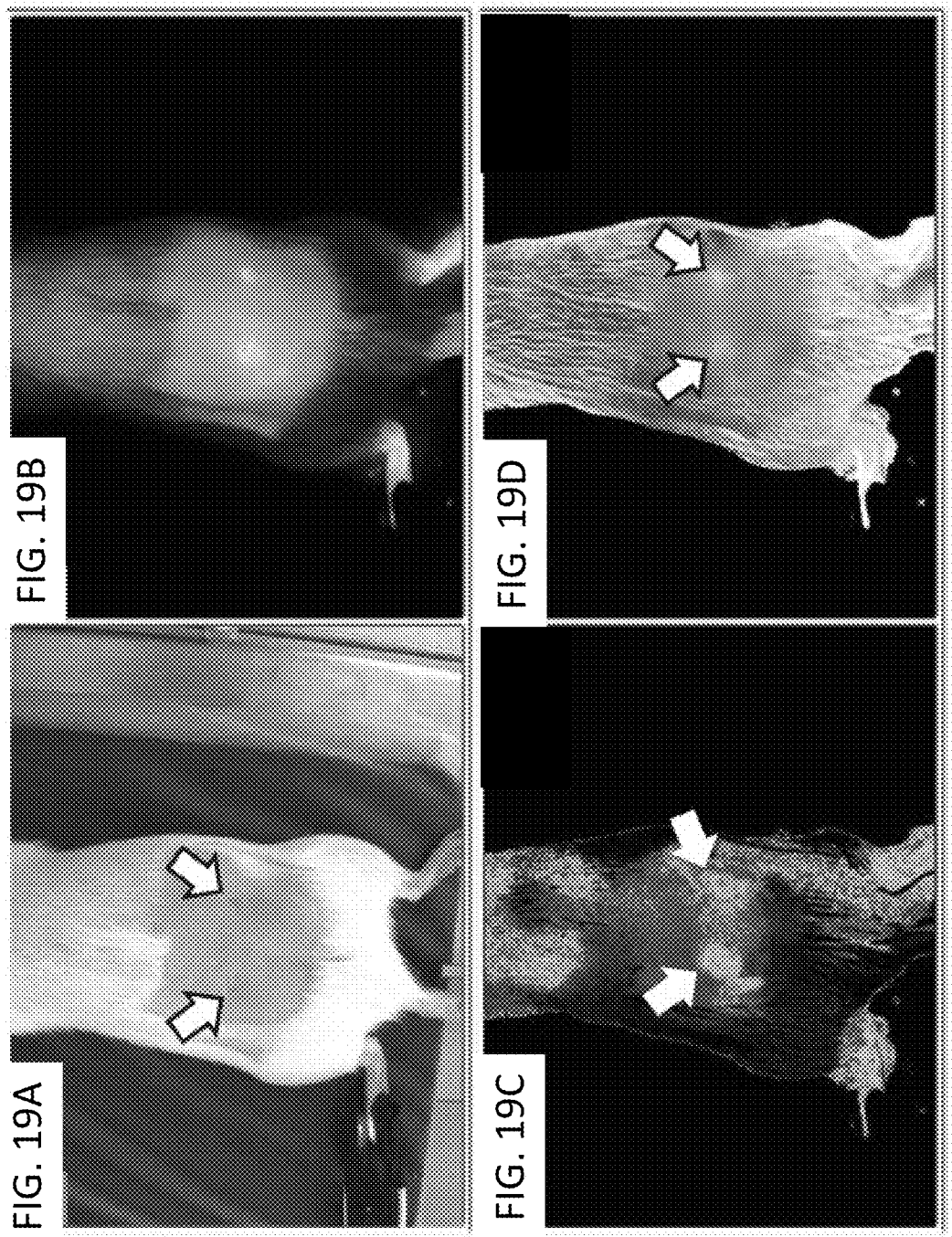

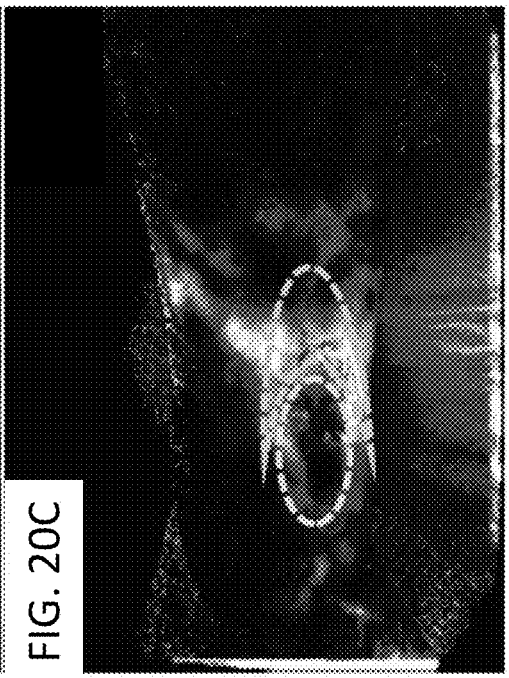

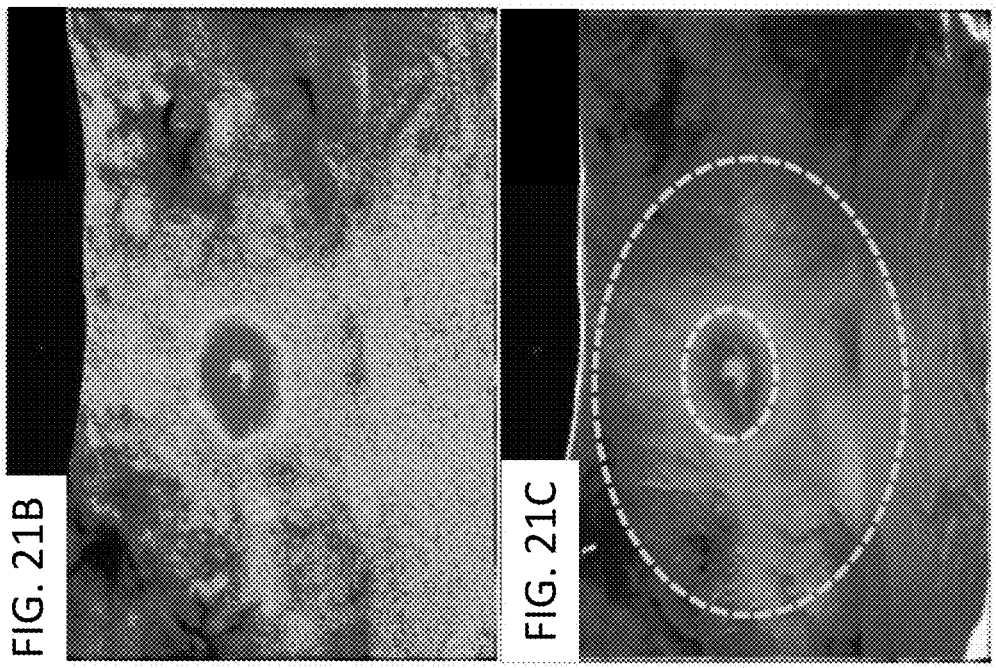
FIG. 21B
FIG. 21C
FIG. 21A

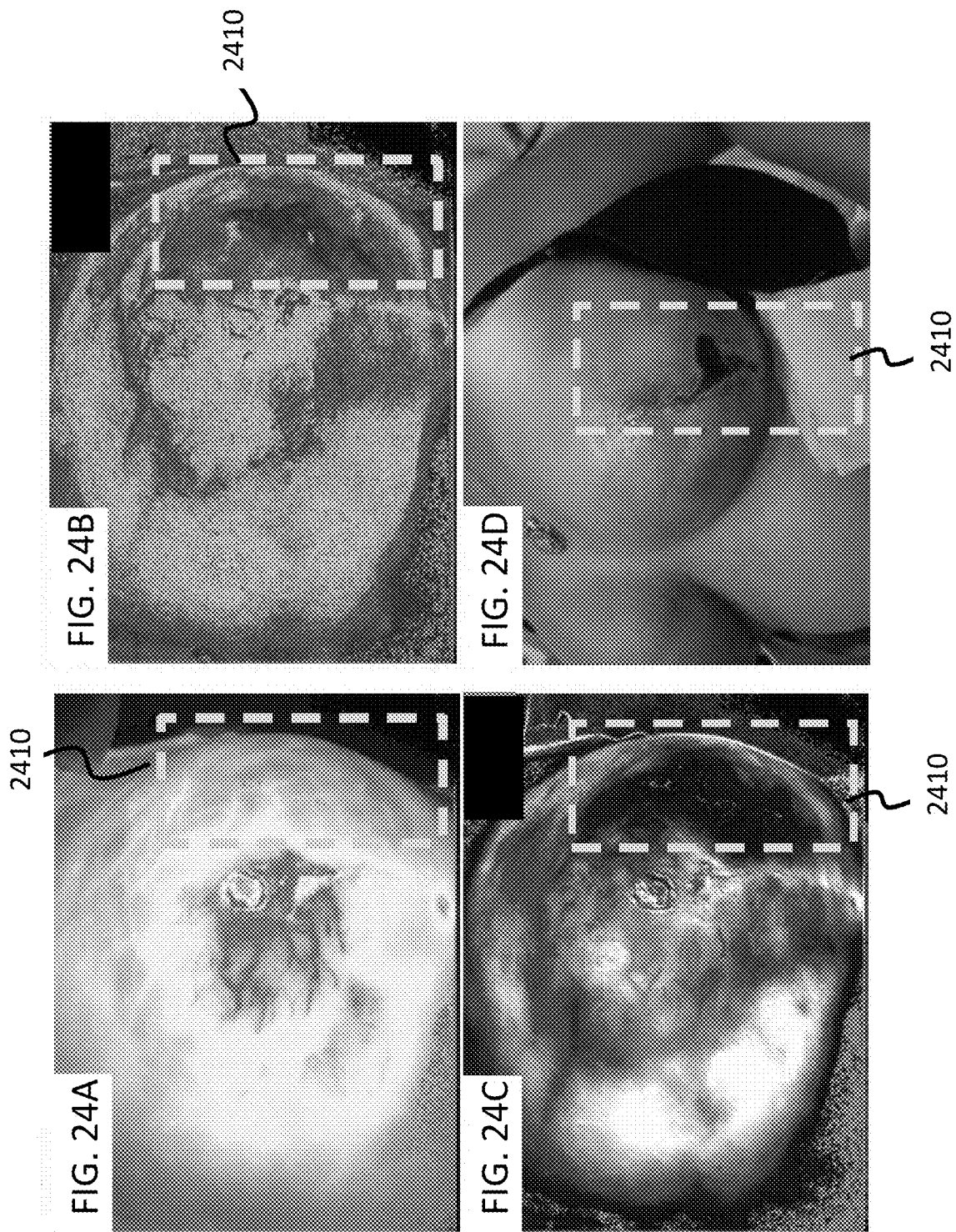

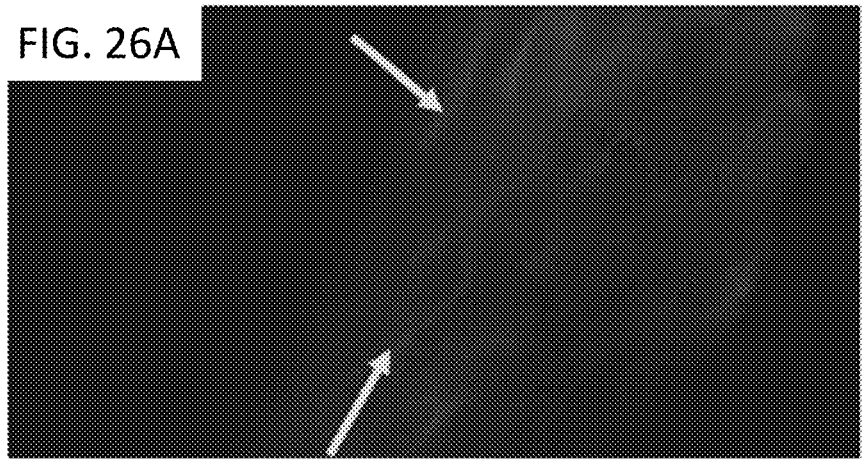
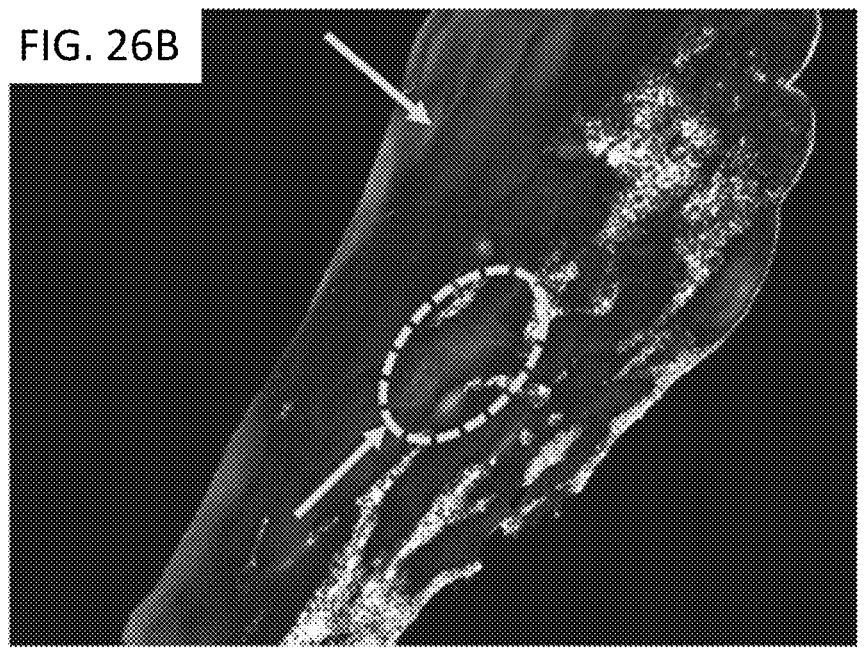

METHODS AND SYSTEMS FOR ASSESSING HEALING OF TISSUE

CROSS-REFERENCE TO RELATED APPLICATIONS

This application is a continuation of U.S. patent application Ser. No. 15/224,088, filed Jul. 29, 2016, which claims priority to U.S. Provisional Application Ser. No. 62/222,630 filed on Sep. 23, 2015, entitled "METHODS AND SYSTEMS FOR ASSESSING TISSUE TO ESTABLISH A PROGNOSIS FOR TISSUE HEALING," both of which are hereby incorporated by reference in their entirety.

BACKGROUND OF THE INVENTION

Poor tissue perfusion has an adverse effect on the healing process of tissue. To increase the chances of determining whether successful healing of, for example, acute and chronic wounds will occur, clinicians must correctly assess blood flow and tissue perfusion in and around the wound site. Furthermore, the ability to predict the potential for healing and the timeline of healing is also important. Usually, visual assessment of the wound, measurement of a reduction in wound area, and/or the percentage of wounds healed within a defined period is used as a scoring system for establishing a wound treatment protocol.

Certain advanced practices have begun to use imaging technologies such as fluorescence imaging technologies for assessing blood flow and/or tissue perfusion and establishing a prognosis for wound healing. Fluorescence imaging technologies may, for example, employ the administration of a bolus of an imaging agent (such as, for example, indocyanine green which binds with blood proteins in a subject) that subsequently circulates throughout the subject's vasculature and emits a fluorescence signal when illuminated with the appropriate excitation light. Fluorescence imaging systems acquire images of the emitted imaging agent fluorescence as the imaging agent bolus traverses the subject's tissue in the field of view. The images are typically acquired as the bolus enters the tissue through arterial vessels, travels through the tissue's microvasculature, and exits the tissue through the venous vessels. When the images are displayed as video on a monitor, clinicians may observe this imaging agent transit in the vasculature represented as variations in fluorescence intensity with time. Based on their visual perception of the fluorescence intensity, clinicians may make a relative, qualitative determination regarding the blood flow and/or perfusion status of the tissue and its subsequent healing potential. However, a qualitative visual evaluation of such images is not always sufficient for a number of reasons, particularly in instances where the visual information is ambiguous. For instance, such visual evaluation is limited since many parameters, such as image brightness, image contrast and image noise, can be affected by factors other than the blood flow and/or perfusion properties of the tissue. Moreover, mere visual evaluation is subjective (e.g., visual evaluation may vary from clinician to clinician, one clinician's visual evaluation protocol may vary somewhat from patient to patient and/or from imaging session to imaging session) and does not support a standardized protocol for assessing blood flow and/or tissue perfusion, and/or for assessing healing of tissue (e.g., progress of healing, efficacy of clinical intervention, etc.). Finally, due to a clinician's lack of memory or inaccurate recollection of previous visual assessments, it can be challenging to reliably and consistently compare and track blood flow, perfusion, and/or healing status of a patient over time across multiple imaging sessions.

The assessment of perfusion dynamics and a prognosis of tissue healing is also important in other clinical applications aside from wound care, such as, for example, pre-surgical evaluation of patients undergoing plastic or reconstructive procedures (e.g., skin flap transfers). For instance, it is desirable for fluorescence imaging systems to possess the data processing capabilities which consider parameters that reflect relevant perfusion dynamics and facilitate providing a prognosis for tissue healing. Furthermore, it is desirable for fluorescence imaging systems to present image data to the clinician in a manner that provides such information in a convenient and easily understood fashion.

It is therefore desirable to provide a tool that can aid the clinician in providing an accurate and reliable prognosis of healing potential of a tissue, chronicity or both. This will assist, for example, in ensuring that a correct diagnosis of the tissue is given, and that appropriate care is provided in a timely manner, therefore improving healing time and patient quality of life, and alleviating economic burden on healthcare systems.

BRIEF SUMMARY OF THE INVENTION

Described herein are variations of systems and methods for assessing healing of tissue of a subject. Generally, in one variation, a system for assessing healing of tissue of a subject includes one or more processors and memory having instructions stored thereon. The instructions, when executed by the one or more processors, cause the system to receive a time series of signal intensity data capturing the transit of an imaging agent through tissue over a period of time, wherein the time series of signal intensity data define a plurality of calculation regions and wherein signal intensity in each calculation region over the period of time may be approximated by a time-intensity curve corresponding to that calculation region. The at least one calculation region may, for instance, be defined by one pixel or voxel. The instructions further cause the system to determine, for each calculation region, a coefficient value that is related to at least a portion of the time-intensity curve corresponding to the calculation region, and to convert the coefficient values across the plurality of calculation regions into a coefficient-derived image map. The system may include a light source that provides an excitation light to induce fluorescence emission from a fluorescence imaging agent in the tissue, and/or an image acquisition assembly that generates the time series of signal intensity data based on the fluorescence emission such as, for example, a time series of fluorescence angiography images based on the fluorescence emission. Furthermore, the system may include a display for displaying the coefficient-derived image map and/or an anatomical image of the tissue. In other aspects, the system may be configured to perform at least a portion of the methods described herein for assessing healing of tissue of a subject.

In some variations, the coefficient value may characterize a shape of the time-intensity curve, or a portion thereof, such as a region of increasing slope of the time-intensity curve (e.g., an arterial phase of the time-intensity curve), a region of decreasing slope of the time-intensity curve (e.g., a venous phase of the time-intensity curve), or a combination thereof. The coefficient values for the calculation regions may be correlated into a coefficient-derived image map based on, for example, a conversion of each of the coefficient values into a respective pixel intensity. The resulting coefficient-derived image map may, in some variations, be indicative of an actual or suspected wound and allow for predictive assessment of healing of tissue of the subject.

Generally, one variation, a method for assessing healing of tissue of a subject includes receiving a time series of signal intensity data capturing the transit of an imaging agent through tissue over a period of time, wherein the tissue comprises a plurality of calculation regions and wherein signal intensity in each calculation region over the period of time may be approximated by a time-intensity curve corresponding to the calculation region, determining for each calculation region a coefficient value that is related to at least a portion of the time-intensity curve corresponding to the calculation, and converting the coefficient values across the plurality of calculation regions into a coefficient-derived image map. The at least one calculation region may, for instance, be defined by one pixel or voxel. The method may be performed at a computer system including one or more processors and memory.

As in the system briefly described above, the coefficient value may characterize a shape of the time-intensity curve, or a portion thereof, such as a region of increasing slope of the time-intensity curve (e.g., an arterial phase of the time-intensity curve), a region of decreasing slope of the time-intensity curve (e.g., a venous phase of the time-intensity curve), or a combination thereof. Converting the coefficient values into a coefficient-derived image map may comprise correlating each coefficient value with an intensity value. The coefficient-derived image map, and/or other images and info such as an anatomical image of the tissue, may be displayed and/or superimposed on one another on a display.

The method may further comprise assessing tissue of the subject based at least in part on the coefficient-derived image map. The assessed tissue may include, for example, a wound and/or peri-wound in the tissue. Assessing the tissue may comprise generating a quantitative predictor of the progress of healing of tissue, efficacy of clinical intervention, or a combination thereof based on at least a portion of the coefficient-derived image. The quantitative predictor may be based on a single coefficient-derived image, though a plurality of coefficient-derived images may be obtained and compared over time (e.g., based on a plurality of time series of signal intensity data captured over time) in order to generated other assessments.

In some variations, the method may further comprise determining, for each calculation region, a second coefficient value that is related to at least a second portion of the time-intensity curve corresponding to the calculation region, and converting the second coefficient values across the plurality of calculation regions into a second coefficient-derived image map. For instance, the first coefficient-derived image map may be an arterial coefficient-derived image map and the second coefficient-derived image map may be a venous coefficient-derived image map. In these variations, assessing tissue of the subject may comprise generating a quantitative predictor of the progress of healing of tissue, efficacy of clinical intervention, or a combination thereof, based on the first and second coefficient-derived image maps. For example, generating the quantitative predictor may comprise comparing the area of a first selected region in the first coefficient-derived image map to the area of a second selected region in the second coefficient-derived image map, where the selected regions represent an actual or suspected wound (or other abnormal or suspected abnormal arterial or venous activity). Accordingly, the quantitative predictor may, for example, include a ratio of the areas of the first and second selected regions.

Additionally, the method may further include generating the time series of signal intensity data using a fluorescence imaging system that captures transit of the imaging agent through tissue over a period of time. For example, the imaging agent may include indocyanine green, fluorescein isothiocyanate, rhodamine, phycoerythrin, phycocyanin, allophycocyanin, ophthaldehyde, fluorescamine, rose Bengal, trypan blue, fluoro-gold, green fluorescence protein, a flavin, methylene blue, porphysomes, cyanine dye, IRDDye800CW, CLR 1502 combined with a targeting ligand, OTL38 combined with a targeting ligand, or a combination thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 9-10 depict images of a control rat that were generated according to an exemplary embodiment. FIGS. 10A-10D depict results for the control rat 48 hours after removal of pressure magnets.

FIGS. 11-13 depict images of a rat with minor wounds induced by pressure magnets, where results were generated according to an exemplary embodiment. FIGS. 11A-11D depict results for the rat 3 hours after removal of pressure magnets. FIGS. 12A-12D depict results for the rat 24 hours after removal of pressure magnets. FIGS. 13A-13D depict results for the rat 48 hours after removal of pressure magnets.

FIGS. 14-19 depict images of a rat with severe wounds induced by pressure magnets, where results were generated according to an exemplary embodiment. FIGS. 14A-14D depict results for the rat immediately after removal of pressure magnets. FIGS. 15A-15D depict results for the rat 2 hours after removal of pressure magnets. FIGS. 16A-16D depict results for the rat 24 hours after removal of pressure magnets. FIGS. 17A-17D depict results for the rat 48 hours after removal of pressure magnets. FIGS. 18A-18D depict results for the rat 72 hours after removal of pressure magnets. FIGS. 19A-19D depict results for the rat 8 days after removal of pressure magnets.

FIGS. 20A-20C depict a color image, an arterial coefficient-derived image, and a venous coefficient-derived image, respectively, for a severe shin ulcer wound, where the images are generated according to an exemplary embodiment relating to an application of the methods and systems to assess healing of tissue.

FIGS. 21A-21C depict a color image, an arterial coefficient-derived image, and a venous coefficient-derived image, respectively, for a traumatic fracture wound, where the images are generated according to an exemplary embodiment relating to an application of the methods and systems to assess healing of tissue.

FIGS. 24A-24C depict a maximum perfusion image, an arterial coefficient-derived image, and a venous coefficient-derived image of breast tissue obtained pre-surgery, where the images are generated according to an exemplary embodiment relating to an application of the methods and systems to plastic and reconstructive surgery. FIG. 24D depicts a color image of the breast tissue post-surgery.

FIGS. 26A and 26B illustrate a maximum perfusion image and a venous coefficient-derived image generated according to an exemplary embodiment relating to an application of the methods and systems to identify a vessel network and discriminate between different kinds of vessels in the network.

DETAILED DESCRIPTION OF THE INVENTION

Reference will now be made in detail to implementations and embodiments of various aspects and variations of the invention, examples of which are illustrated in the accompanying drawings.

One challenge in wound management, (e.g., chronic wound management) is that the medical condition or nature of a wound can be viewed differently among clinicians depending, for example, on the skill and experience of the clinician. Current techniques may provide information about the wound's pathological history, but fail to provide reliable indicators of viability and/or restorative potential, e.g., whether wound and/or peri-wound (i.e., tissue surrounding the wound or adjacent the wound) is likely to develop complications, is capable of healing, how healing progresses, and whether the treatment applied is effective and when it can be discontinued. Furthermore, wounds exist where no pathology is demonstrable by conventional diagnostic techniques. Various embodiments of the methods and systems of the present invention facilitate producing a consistent representation (not subjective to biases of perception) of the state of a particular target tissue (e.g. wound, peri-wound), and thus facilitate a more accurate, consistent assessment and formulation of care strategies (e.g., recommendation and assessment of efficacy of care such as, for example, topical treatments, hyperbaric oxygen therapy, assessment of the tissue pre- and post-surgery, formulation of surgical strategy).

The methods and systems described herein may, for example, be used in wound management, plastic surgery, and/or reconstructive surgery. Examples of uses include assessment of the wound and peri-wound environments in the tissue, discrimination between healing and non-healing wounds, assessment of a state of the wound, a property of the wound, a condition of the wound, and/or a healing status of the wound. The wound may be, for example, a surgical wound, a chronic wound, and/or an acute wound. Examples of such wounds include incisions, pressure ulcers, venous ulcers, arterial ulcers, diabetic lower extremity ulcers, lacerations, abrasions, punctures, contusions, avulsions, cavities, burns, other injury, or any combination thereof.

Methods for Assessing Healing of Tissue

Figure 1:
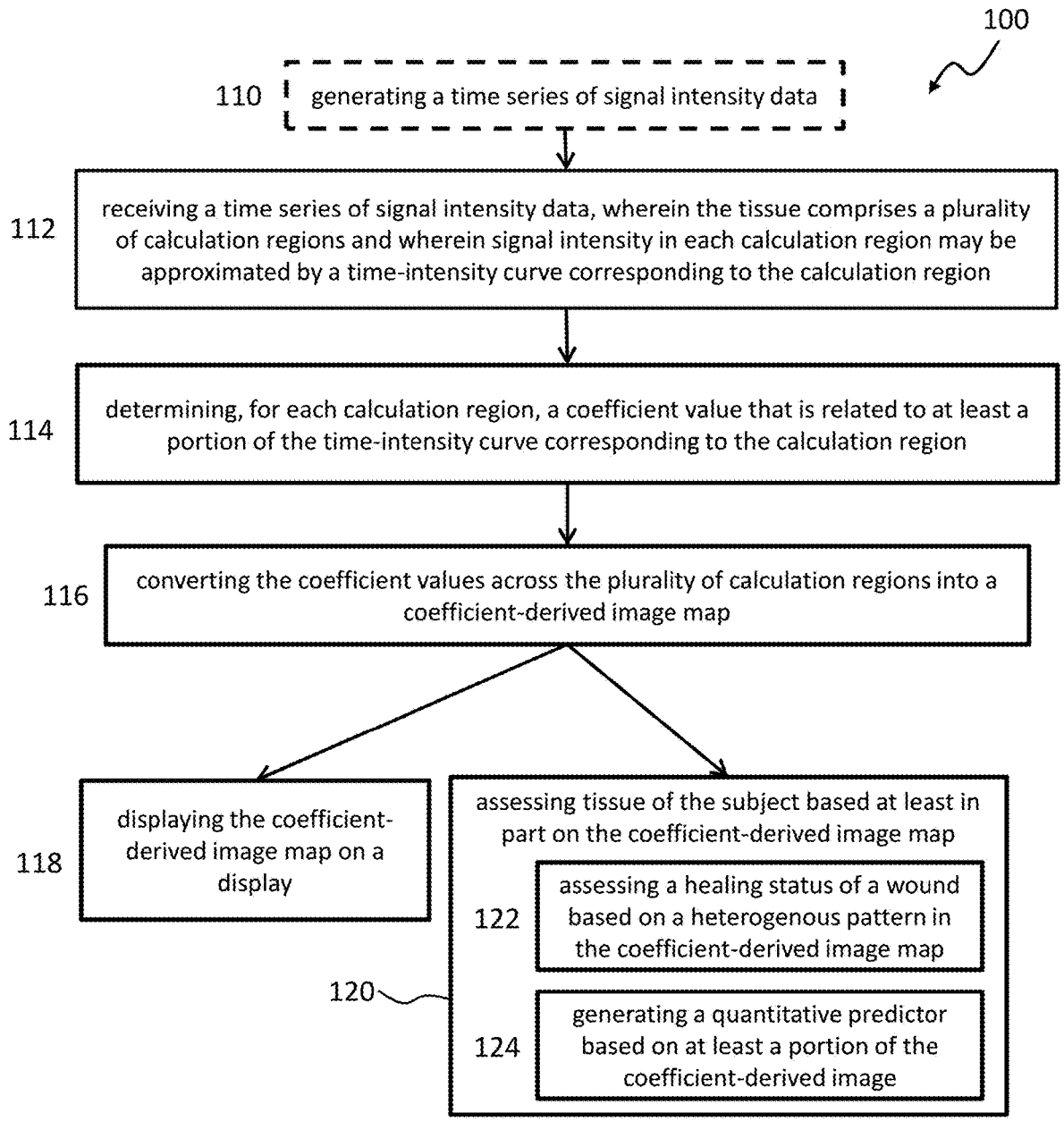
FIG. 1 is an illustrative block diagram of an exemplary method for assessing healing of tissue of a subject.

As shown in FIG. 1, an example of a method 100 for assessing healing of tissue may include: receiving a time series of signal intensity data 112 capturing the transit of an imaging agent through tissue over a period of time, wherein the tissue comprises a plurality of calculation regions and wherein signal intensity in each calculation region over the period of time may be approximated by a time-intensity curve corresponding to the calculation region; determining, for each calculation region, a coefficient value 114 that is related to at least a portion of the time-intensity curve corresponding to the calculation region; and converting the coefficient values across the plurality of calculation regions into a coefficient-derived image map 116. The method 100 may further include displaying the coefficient-derived image map on a display 118 and/or assessing tissue of the subject based at least in part on the coefficient-derived image map 120.

At least a portion of the method may be performed by a computer system located separate from a medical imaging system. For instance, some or all of the steps of receiving a time series of signal intensity data 112, determining for each calculation region a coefficient value 114, converting the coefficient values across the plurality of calculation regions into a coefficient-derived image map 116, and/or assessing tissue of the subject based at least in part on the coefficient-derived image map 120 may be performed by a computer system at an off-site location that is remote from a clinical site (e.g., where a fluorescence imaging system is situated) or by a computer system that is located at a clinical setting but not embodied in an imaging system. In these variations, the time series of signal intensity data may be received as a result of a transfer of signal data from a data storage medium (e.g., hard drive, cloud storage, etc.) or through a network communication (e.g., wired connection, Internet, wireless network based on a suitable wireless technology standard, etc.). For instance, the method may involve a client-server architecture, such that an imaging system may include client hardware that sends signal data to a computing server and loads processed data (e.g., coefficient-derived image map or interim outputs of various steps of the methods described herein) back onto the imaging system. After the client hardware in the imaging system loads the processed data, the imaging system may further process the data and/or display the processed data in accordance with the methods described herein.

In some variations, at least a portion of the method is performed by one or more processors at a computer system incorporated into a medical imaging system, such as at a clinical site. For example, some or all of the steps of receiving a time series of signal intensity data 112, determining for each calculation region a coefficient value 114, converting the coefficient values across the plurality of calculation regions into a coefficient-derived image map 116, and/or assessing tissue of the subject based at least in part on the coefficient-derived image map 120 may be performed by a computer system in a medical imaging system. In some of these variations, the method may further include generating the time series of signal intensity data 110 prior to receiving the time series of signal intensity data.

As described above, current medical imaging technologies such as fluorescence imaging systems provide limited opportunity for clinicians to accurately assess blood flow and/or tissue perfusion in tissue of a subject. For instance, when visually evaluating fluorescence images that capture transit of a dye bolus through tissue, clinicians' assessment of blood flow and/or tissue perfusion is confounded by parameters (e.g., brightness, image contrast, image noise) that are independent of perfusion properties of the tissue. Additionally, clinicians' mere visual evaluation of the images is subjective and may vary from clinician to clinician, patient to patient, and/or imaging session to imaging session. Furthermore, due to a clinician's lack of memory or inaccurate recollection of previous visual assessments, there is no way to reliably and consistently compare and track blood flow and/or perfusion status of a patient over time across multiple imaging sessions.

The methods and systems described herein for assessing healing of tissue process and present data to the user in a manner that enables more effective clinical decision making. For instance, the one or more coefficient-derived image maps may be spatial maps that concisely shows relative differences between different regions of tissue, with respect to dynamic behavior of an imaging agent in the tissue. For example, the coefficient-derived image map may be a visualization of how different areas of the tissue vary in healing status, tissue property, and/or other tissue condition (e.g., inflammation, malignancy, disease, other abnormality, or a combination thereof, etc.) in a manner that is easily perceptible and identifiable by a human being. As described further herein, these quantified visualizations reduce ambiguity and the effect of clinicians' subjectivity, by facilitating a standardized protocol for assessing blood flow and/or perfusion and/or assessing healing of tissue. Thus, these quantified visualizations enable a clinician to make more consistent clinical assessments and/or medical treatment decisions. Furthermore, assessment of progress of healing and other assessments may be derived, at least in some circumstances, from content of a single coefficient-derived image map where other imaging modalities (e.g., color images visualizing the external surface of the tissue) fail to enable such assessments.

Although various exemplary embodiments are described in the specification in the context of a time series of fluorescence images, the method may be applied to other sources of images generated as a time series which relate to a dynamic behavior of an imaging agent in the tissue and for other clinical purposes. For example, the images may be derived from computerized tomographic (CT) angiography with a radio-opaque contrast dye for blood flow and tissue perfusion assessment. As another example, the images may be derived from positron emission tomography (PET) using a fluorodeoxyglucose (FDG) or other radiotracer to evaluate metabolic activity and potentially assess pathology and/or provide information usable for assessing pathology. As another example, the images may be derived from contrast-enhanced ultrasound imaging employing the use of gas-filled microbubble contrast medium administered intravenously to the systemic circulation. Such ultrasonic imaging using microbubble contrast agents enhances the ultrasound backscatter or reflection of the ultrasound waves to produce a unique sonogram with increased contrast due to the high echogenicity (i.e., ability of an object to reflect the ultrasound waves) difference between the gas in the microbubbles and the soft tissue. Contrast-enhanced ultrasound can be used, for example, to image blood perfusion and blood flow in organs.

Generating the Time Series of Signal Intensity Data

As shown in FIG. 1, the method may include generating a time series of signal intensity data 110. The time series of signal intensity data of the tissue of the subject may include fluorescence images or video (or representative thereof) generated by fluorescence imaging technologies employing a fluorescence imaging agent such as, for example, indocyanine green (ICG) dye as a fluorescence imaging agent. ICG, when administered to the subject, binds with blood proteins and circulates with the blood in the tissue. Although reference is made in the specification to a fluorescence imaging agent or a fluorescence dye, other suitable imaging agents may be used depending on the type of imaging technology being employed to generate the time series of signal intensity data.

In some variations, the fluorescence imaging agent (e.g., ICG) may be administered to the subject as a bolus injection, in a suitable concentration for imaging. In some variations where the method is performed to assess tissue perfusion, the fluorescence imaging agent may be administered to the subject by injection into a vein or artery of the subject such that the dye bolus circulates in the vasculature and traverses the microvasculature. In some variations in which multiple fluorescence imaging agents are used, such agents may be administered simultaneously (e.g., in a single bolus), or sequentially (e.g., in separate boluses). In some variations, the fluorescence imaging agent may be administered by a catheter. In some variations, the fluorescence imaging agent may be administered to the subject less than an hour in advance of performing the measurements for generating the time series of fluorescence images. For example, the fluorescence imaging agent may be administered to the subject less than 30 minutes in advance of the measurements. In other variations, the fluorescence imaging agent may be administered at least 30 seconds in advance of performing the measurements. In some variations, the fluorescence imaging agent may be administered contemporaneously with performing the measurements.

In some variations, the fluorescence imaging agent may be administered in various concentrations to achieve a desired circulating concentration in the blood. For example, in some variations for tissue perfusion assessment where the fluorescence imaging agent is ICG, the fluorescence imaging agent may be administered at a concentration of about 2.5 mg/mL to achieve a circulating concentration of about 5 µM to about 10 µM in blood. In some variations, the upper concentration limit for the administration of the fluorescence imaging agent is the concentration at which the fluorescence imaging agent becomes clinically toxic in circulating blood, and the lower concentration limit is the limit for instruments used to acquire the time series of signal intensity data that detect the fluorescence imaging agent circulating in blood. In some variations, the upper concentration limit for the administration of the fluorescence imaging agent is the concentration at which the fluorescence imaging agent becomes self-quenching. For example, the circulating concentration of ICG may range from about 2 µM to about 10 mM.

Thus, in one aspect, the method may comprise administration of a fluorescence imaging agent or other imaging agent to the subject, and generation or acquisition of the time series of fluorescence images prior to processing the image data. In another aspect, the method may exclude any step of administering the fluorescence imaging agent or other imaging agent to the subject. For instance, the time series of fluorescence images may be based on measurements of a fluorescence imaging agent such as, for example, indocyanine green (ICG) dye that is already present in the subject and/or based on autofluorescence response (e.g., native tissue autofluorescence or induced tissue autofluorescence), or measurements of a combination of autofluorescence and exogenous fluorescence arising from a fluorescence imaging agent.

In some variations, a suitable fluorescence imaging agent is an agent which can circulate with the blood (e.g., a fluorescence dye which can circulate with a component of the blood such as lipoproteins or serum plasma in the blood) and which fluoresces when exposed to appropriate excitation light energy. The fluorescence imaging agent may comprise a fluorescence dye, an analogue thereof, a derivative thereof, or a combination of these. A fluorescence dye may include any non-toxic fluorescence dye. In some variations, the fluorescence imaging agent optimally emits fluorescence in the near-infrared spectrum. In some variations, the fluorescence imaging agent is or comprises a tricarbocyanine dye such as, for example, indocyanine green (ICG). In other variations, the fluorescence imaging agent is or comprises fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, or a combination thereof, which is excitable using excitation light wavelengths appropriate to each imaging agent. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations in which some or all of the fluorescence is derived from autofluorescence, one or more of the fluorophores giving rise to the autofluorescence may be an endogenous tissue fluorophore (e.g., collagen, elastin, NADH, etc.), 5-aminolevulinic Acid (5-ALA), or a combination thereof.

In some variations, the fluorescence imaging agent may be provided as a lyophilized powder, solid, or liquid. The fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. Any diluent or carrier which will maintain the fluorescence imaging agent in solution may be used. As an example, ICG may be reconstituted with water. In some variations, once the fluorescence imaging agent is reconstituted, it may be mixed with additional diluents and carriers. In some variations, the fluorescence imaging agent may be conjugated to another molecule, (e.g., a protein, a peptide, an amino acid, a synthetic polymer, or a sugar) so as to enhance solubility, stability, imaging properties or a combination thereof. Additional buffering agents may optionally be added including Tris, HCl, NaOH, phosphate buffer, HEPES.

The time series of signal intensity data may comprise a plurality of individual image frames (e.g., fluorescence image frames), or data representative of individual frames, ordered consecutively by acquisition time. For example, a time series of signal intensity data can be acquired using an ICG-based fluorescence imaging system, where the subject receives an intravenous injection of ICG immediately prior to procedure, and the tissue is illuminated with light at ICG's excitation wavelengths while the resulting fluorescence emission from the dye as it transits the target tissue is imaged. The fluorescence images may subsequently be stored as a series of individual frames, or signal intensity data representative of individual frames (e.g., compressed video), ordered consecutively by their acquisition time.

In some variations, the individual image frames of the time series are spatially aligned or registered. For example, a typical time series of fluorescence images may be recorded over 2 to 3 minutes, during which some subjects' movements may be unavoidable. As a result, the same anatomical features can appear at different positions in image frames acquired at different times during the image time series acquisition period. Since such misalignments can introduce errors in the subsequent analysis where the level of fluorescence for each pixel or a group of pixels is followed over time. To help reduce errors, the generated image frames may be spatially aligned (registered) with each other. In some variations, image registration or alignment refers to a process of determining the spatial transform that maps points from one image to homologous points in the second image.

Image registration may be an iterative process. For example, according to an exemplary embodiment, image registration may use one or more of the following set of components: two input images, a transform, a metric, an interpolator, and an optimizer. A transform maps the fixed image space into the moving image space. An optimizer is required to explore the parameter space Insight Segmentation and Registration Toolkit (ITK) (http://itk.org/) based implementation of the transform in search of optimal values of the metric may be used. The metric compares how well the two images match each other. Finally, the interpolator evaluates the intensities of the moving image at non-grid positions. To align the entire time series of fluorescence images, this procedure is executed for all the frames included in the analysis. The component loops through the range of input series frames, subtracts a background image for baseline correction and applies noise-reduction filters, then registers consecutive pairs of images.

In some variations, the time series of fluorescence images is pre-processed to, for example, extract selected data, calculate a baseline intensity, perform an image quality improvement process, or a combination thereof.

Extraction of selected data may, for example, comprise cropping to locate and exclude certain data from the image time series data. For example, during a fluorescence imaging procedure of the subject, an operator might start recording the time series of fluorescence images (or signal intensity data) well before the fluorescence imaging agent reaches the target tissue As a result, the time series of fluorescence images might have a significant number of "dark" frames in the beginning, thus adding unnecessary computational time for the frames that contain no meaningful data. To mitigate the problem, cropping can be used to remove those "dark" frames from the beginning of the time series of fluorescence images. In addition, when the subject is injected with the fluorescence imaging agent (e.g., ICG), the fluorescence signal from the imaging agent as it transits the target tissue typically proceeds through a series of phases: rapid increase of fluorescence intensity as the imaging agent enters the tissue through arterial vessels, followed by a period of stable fluorescence as the imaging agent traverses the microvasculature, then slow decrease in fluorescence intensity due to the venous outflow of the imaging agent, followed by a period of residual fluorescence as any imaging agent retained in the lining of the vasculature released into the bloodstream. This last "residual" phase can last for several minutes and, as it is not directly indicative of blood flow, does not typically provide meaningful perfusion information. Thus, cropping may be used to locate and exclude the residual phase from subsequent steps of analysis.

In some variations, pre-processing may include calculation of the baseline intensity. For example, when the time series of fluorescence images is being generated by a fluorescence imaging system, various external factors can contribute to the fluorescence of the recorded series, such as camera noise, thermal noise, and/or presence of residual fluorescence dye from an earlier injection. In order to minimize the influence of such factors on the analysis, the baseline intensity may be calculated for every series, and the analysis of the data may be adjusted accordingly.

In some variations, pre-processing may include an image quality validation process. Such a process may comprise a starting brightness test in embodiments where, for example, the acquisition of the time series of fluorescence images has started too late and the imaging agent has already begun its transit of the target tissue by the time the first frame was captured. In this scenario, the time series of fluorescence images cannot be reliably analyzed or processed since the information relating to the start of perfusion has been lost. As a result, such series data would be rejected.

In some variations, the image quality validation process may comprise a brightness change test. Such a test may be used, for example, in instances where the fluorescence imaging system was suddenly moved during the image acquisition, foreign objects appeared in the field of view, or a light from an external source illuminated the scene while the series was being captured. All of these events may significantly distort the results of any subsequent analysis. Accordingly, the time series of fluorescence images or signal intensity data subjected to such a test might fail the validation procedure (be identified as being unsuitable for further processing). According to an exemplary embodiment, the brightness change test comprises a calculation of the difference between average intensities of neighboring frames in the time series of fluorescence images and compares it to a selected intensity difference threshold. In order to pass validation, the differences in intensities of all consecutive frames must be within the limit specified by the selected intensity difference threshold.

In some variations, the image quality validation process may comprise an intensity peak location test to check that the acquisition of the time series of fluorescence images has not been stopped prematurely. For example, the intensity peak location test ensures that a sufficient number of frames have been acquired to cover all phases of the dye bolus transit through the tissue. According to an exemplary embodiment, the fluorescence intensity peak location test comprises finding the frame with the maximum average fluorescence intensity and verifying that it is not the last frame in the time series of fluorescence images. Should this condition fail, it will be a strong indication that the fluorescence intensity values have not reached their maximum yet and such a time series of fluorescence images is not suitable for further analysis.

In some variations, the image quality validation process may yet further comprise a maximum fluorescence intensity test. The purpose of the test is to filter out the time series of fluorescence images in which the images are too dark (majority of pixels fall below a pre-defined threshold) or over-saturated (majority of pixels are above a pre-defined saturation threshold).

The curvature of the tissue surface, excessive movement during the image acquisition procedure, dark or oversaturated images, foreign objects within imaged area and external light or shading can affect the quality of the time series of fluorescence images, and thus the subsequent processing of such signal intensity data. To mitigate these problems, a well-structured imaging protocol and a fluorescence imaging system designed to minimize such issues may be used.

The time series of signal intensity data or images may define a plurality of calculation regions. Each calculation region may be an image element such as, for example, a single pixel or group of pixels, a voxel or group of voxels, or some other spatially defined area or volume in the time series of fluorescence images. Each calculation region may be identical in size to all other calculation regions, or may be different in size compared to some or all other calculation regions. In one variation, the boundaries and/or distribution of one or more calculation regions may be pre-defined (e.g., a calculation region for each pixel or voxel, or a calculation region for each 2×2 group of pixels or 2×2×2 block of voxels). In another variation, the boundaries and/or distribution of one or more calculation regions may be defined by a user such as the clinician.

Determining Coefficient Values

Figure 2A:
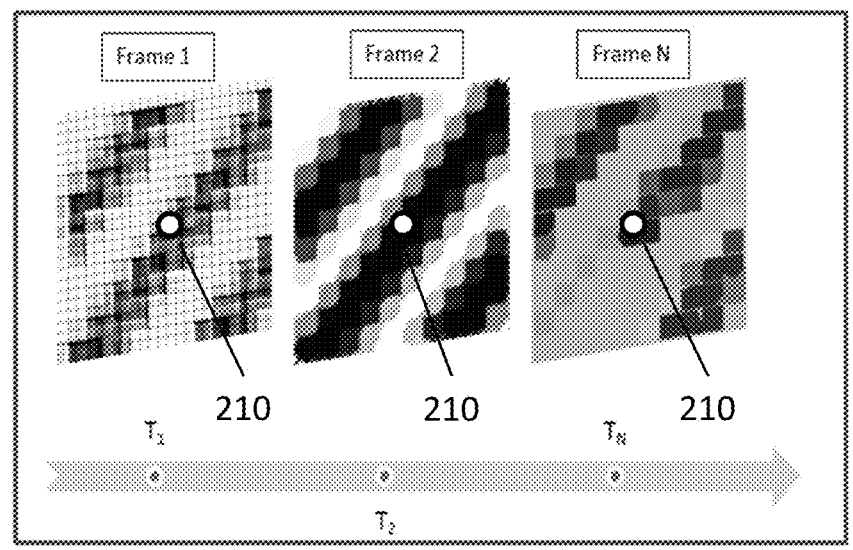
FIG. 2A is an illustrative depiction of a time series of images.

As shown in FIG. 1, the method may include determining, for each calculation region, a coefficient value 114 that is related to at least a portion of the time-intensity curve corresponding to the calculation region. As shown schematically in FIGS. 2A and 2B, a given time-intensity curve 212 (FIG. 2B) corresponding to a particular calculation region 210 (FIG. 2A) describes the intensity of fluorescence signal observed in that calculation region throughout the time series of fluorescence signal intensity data. In some variations, a time-intensity curve describes all phases (e.g. arterial, micro-vascular, venous and residual in angiography applications), a subset of a phase or of a combination of phases, a subset of all phases, or a derivative thereof (including, for example, determinations based upon first and second time derivatives associated with changes in fluorescent intensity on a pixel-by-pixel, or voxel-by-voxel, basis). All or some of the time-intensity curves may be generated by a processor embodied in a fluorescence imaging system that generated the fluorescence images, or by a processor remote from the fluorescence imaging system that generated the fluorescence images.

Figure 2B:
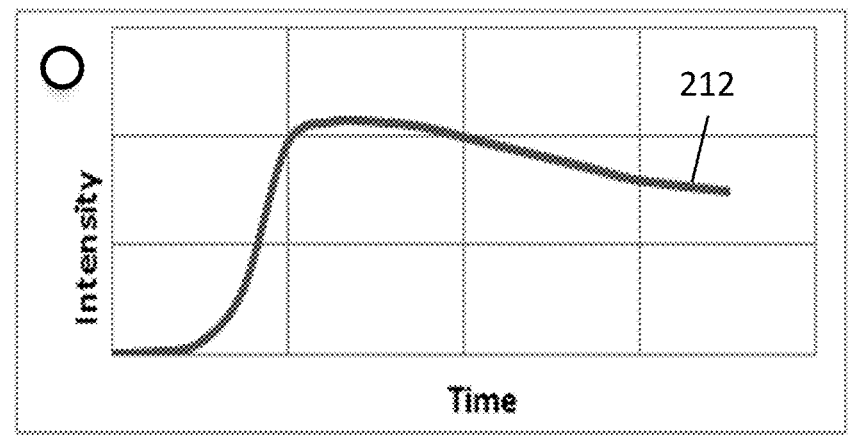
FIG. 2B is an illustrative depiction of a time-intensity curve generated for a calculation region in the time series of images.
Figure 3:
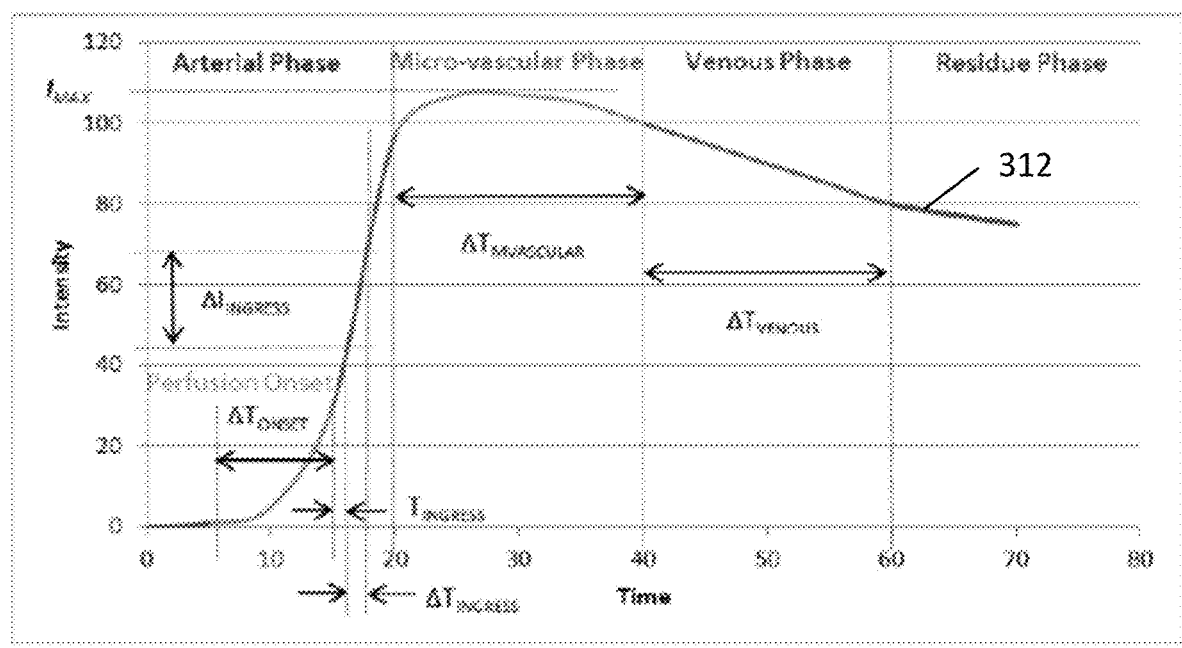
FIG. 3 is an exemplary time-intensity curve with a plurality of exemplary parameters that approximate or otherwise characterize the time-intensity curve.

In some variations, as shown in FIG. 2B, a time-intensity curve 212 comprises a region of increasing intensity, a region of peak intensity, a plateau region, a region of decreasing intensity, or a combination thereof. In the context of fluorescence imaging (e.g., fluorescence angiography), as shown in FIG. 3, a time-intensity curve 312 may represent the transit of a fluorescence imaging agent (e.g., a fluorescence dye) bolus through the tissue as a series of phases: an arterial phase, a micro-vascular phase, a venous phase, a residual phase, or a combination thereof. The shape of the time-intensity curve (or a portion thereof), an area under the time-intensity curve, or a combination thereof may be indicative of distribution of the fluorescence imaging agent in the tissue of the subject, blood flow in the tissue, or a combination thereof. In some applications, the distribution of the imaging agent in the tissue of the subject represents a property of the tissue, a condition of the tissue (e.g., inflammation, malignancy, abnormality, disease) or a combination thereof.

In some variations, the coefficient values for the calculation regions may characterize a shape of at least a portion of the time-intensity curve. For instance, a coefficient value may characterize a region of increasing slope of the time-intensity curve (e.g., arterial phase of the time-intensity curve, or a region correlating to a time period between a start time of measurement of the transit of the imaging agent through the tissue and time of maximum signal intensity, etc.), a region of decreasing slope of the time-intensity curve (e.g., a venous phase of the time-intensity curve, or a region correlating to a time period between a time of maximum signal intensity and an end time of measurement of the transit of the imaging agent through the tissue), or a combination thereof.

In some variations, the coefficient values are related to a mathematical model which approximates a signal intensity arising from the imaging agent that circulates with blood and transits vasculature of the tissue as a function of time. In one exemplary embodiment relating to fluorescence imaging using, for example, ICG as the imaging agent, the coefficient values may be related to, for example, the mathematical model in Formula 1 disclosed in Eren et al. in Assessment of Microcirculation of an Axial Skin Flap Using Indocyanine Green Fluorescence Angiography, Plastic and Reconstructive Surgery, December 1995, pp. 1636 to 1649 (hereinafter referred to as "Eren"), which is incorporated herein by reference. One skilled in the art will appreciate that the mathematical model described in connection with Formula 1 is exemplary only, and may be further modified to approximate the transit of the imaging agent in the tissue, or replaced by a different functionally-equivalent mathematical model.

$$f(t) = f_{Max}\left(1 - e^{-\frac{t'}{C_{Inf}}}\right)e^{-\frac{t'}{C_{Eff}}} \quad \text{Formula 1}$$

where
$f_{Max}$=maximum intensity;
$t'=t-t_{Lag}$;
$t_{Lag}$=influx lag time (the time it takes for the dye to arrive from the site of bolus injection to the region of interest);
$C_{Inf}$=influx (arterial) coefficient or time constant; and
$C_{Eff}$=efflux (venous) coefficient or time constant.

Although Eren postulated the mathematical model of Formula 1, such a model was merely taught in Eren to generate numerical and histogram data relating to the influx and efflux coefficients or time constants. The data reported by Eren in its various tables or histograms is largely devoid of any clinically-meaningful insights. In particular, Eren failed to suggest or appreciate, based on the generated data, that the data could itself be further utilized or transformed for purposes of generating a new image of the tissue (e.g., an arterial coefficient-derived image map and/or a venous coefficient-derived image map of the tissue), and that such new coefficient-derived image of the tissue, if so generated, would provide the user with meaningful visual and quantitative insight into the healing of the tissue (e.g., visual insight as to the pattern of changes in the wound and the wound healing process, and quantitative insight based on the change in the areas of the visual pattern over time). Eren further failed to appreciate that each of such new coefficient-derived images, (e.g., the arterial coefficient-derived image and the venous coefficient-derived image), and in particular the patterns in such images, alone or in a synergistic combination provide particular qualitative and quantitative insight into predicting the potential for healing of the wound tissue. For example, Eren failed to appreciate that the venous coefficient-derived image alone is highly specific in its predictive and diagnostic value although can vary based on a particular clinical application. Similarly, Eren failed to recognize the clinical diagnostic and predictive value of generating spatial maps or images of the tissue based upon such coefficient-derived values, which uniquely facilitate visualization of the dynamic perfusion patterns associated with the wound healing process (e.g., comparing the relative size and shape of the spatially-mapped areas corresponding to the venous coefficient-derived image and the arterial coefficient-derived image, as well as their mutual positions with respect to one another over time, which provide both qualitative and quantitative indications as to the relative status and extent of the wound healing process). Eren further failed to suggest or appreciate that such coefficient-derived maps or images, such as the venous coefficient-derived map or image, could be used to visualize a vessel network and discriminate between different vessels in the network.

In accordance with the exemplary method utilizing Formula 1, a coefficient value (e.g., Cliff, $C_{Eff}$) is calculated at one or more points on the tissue (e.g., for an image element such as, for example, a pixel or a group of pixels) using empirical signal intensity data for the imaging agent in the tissue, where the empirical signal intensity data comprises a set of intensity values over time. According to an embodiment, calculation of $C_{Inf}$ may be performed using Formula 2.

$$g(t)=\log\,[f(t)-f\max]\,\text{where}\,t<t\max \quad \text{Formula 2}$$

Following the calculation of the logarithm of the data, linear regression may be used to derive a straight line, where the slope of the straight line provides the influx (arterial) coefficient value. The efflux (venous) coefficient value is similarly obtained, but without the subtraction of fmax.

In some variations, empirical signal intensity data may include data from empirical sources such as, for example, purely experimental and/or clinical data, data derived from purely experimental/clinical data, or a combination thereof. According to an embodiment, in the mathematical model represented by Formula 1, where the coefficient approximates the shape of the time-intensity curve, $C_{Inf}$ represents the region of increasing slope of the time-intensity curve, and $C_{Eff}$ represents the region of decreasing slope of the time-intensity curve.

Converting the Coefficient Values into a Coefficient-Derived Image Map

As shown in FIG. 1, the method may include converting the coefficient values 116 across the plurality of calculation regions into a coefficient-derived image map. The resulting coefficient-derived image map visualizes the differences in the dynamic behavior of the imaging agent among different regions of the tissue of the subject, and further may provide a visual representation of external and/or internal topography of the tissue. Thus, the coefficient-derived image map may highlight different characteristics of the tissue in an objective, easily understood manner, and may represent a qualitative profile of the tissue. As further described above, as a result, the coefficient-derived image map may facilitate assessment of healing of the tissue (e.g., progress of healing, efficacy of clinical intervention, etc.).

Converting the coefficient values 116 into a coefficient-derived image map may include correlating each coefficient value to an intensity value, such that the calculation regions in the coefficient-derived image map may be depicted with varying intensity values corresponding to the coefficient values. The conversion may involve assigning a display brightness value to each coefficient value wherein the coefficient value and brightness value are in a direct relationship (e.g., the higher the coefficient value, the higher the pixel's intensity). The direct relationship may be linear or nonlinear. In other variations, the conversion may be based on an indirect relationship between the coefficient value and brightness value.

In some variations, the coefficient value may be mapped to a gray scale or a color scale value. For example, the coefficient values may be mapped to an 8-bit grayscale display value (e.g., from 0 to 255), allowing for a grayscale image representation of the coefficient values. In some variations, to optimize visual perception, a color scheme can be applied to the grayscale image representation with different grayscale value ranges represented in appropriately contrasting colors (such as a false color or pseudo color). Other scales may additionally or alternatively be applied to convert the coefficient values into pixel values for the coefficient-derived image map, such that the differences in pixel values reflect the relative differences in coefficient values and among different regions of the imaged tissue.

In another variation, the arterial and venous coefficients may be mathematically pair-wise combined to produce a plurality of combined coefficients, and the combined coefficients may be converted into a coefficient-derived image map. By way of example, one or more combined coefficients may be derived by a weighting of the relative contributions of each of the arterial and venous coefficients, deriving a differential between the arterial and venous coefficients, and/or a summing of the arterial and venous coefficients, etc.

Figure 4:
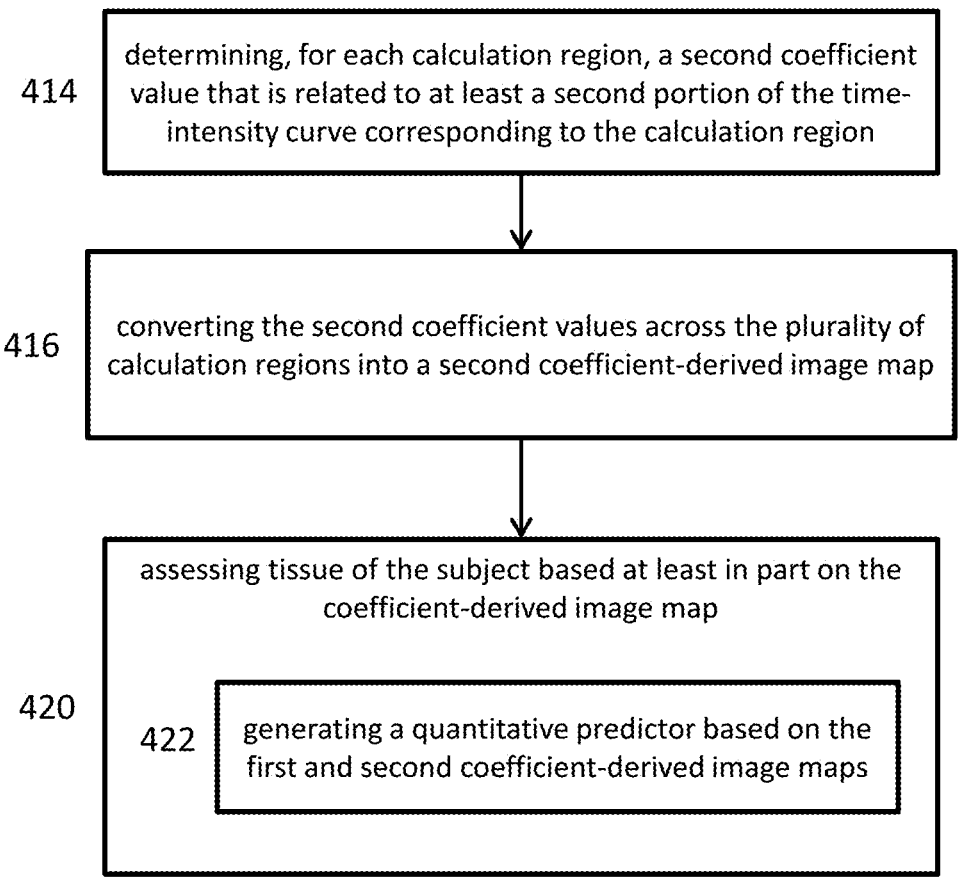
FIG. 4 is an illustrative block diagram of another exemplary method for assessing healing of tissue of a subject.

In some variations, the method may include generating at least two coefficient-derived image maps. For instance, as shown in FIG. 4, the method may include determining, for each calculation region, a second coefficient value 414 that is related to at least a second portion of the time-intensity curve corresponding to the calculation region, and converting the second coefficient values 416 across the plurality of calculation regions into a second coefficient-derived image map. For example, the first coefficient-derived image map may be an arterial coefficient-derived image map (e.g., based on $C_{Inf}$ coefficient values using Formulas 1 and 2) and the second coefficient-derived image map may be a venous coefficient-derived image map (e.g., based on $C_{Eff}$ coefficient values using Formulas 1 and 2).

Assessing Tissue of the Subject Based at Least in Part on the Coefficient-Derived Image Map It was surprisingly found, based on animal and human data, that the process of spatially-mapping the coefficient values to an image map provides a highly useful qualitative and/or a quantitative predictor of the tissue's healing potential and healing state. The external and internal topography features in the coefficient-derived image of the tissue facilitate enhancement and identification of features of the tissue that may not be apparent or visible from a white light image and/or maximum perfusion image of the target anatomy or a numerical representation of the coefficient data relating to the tissue, as is further described below in the examples.

As shown in FIG. 1, the method for assessing healing of tissue of a subject may include assessing tissue of the subject based at least in part on the coefficient-derived image map 120. For instance, the coefficient-derived image may be used alone to assess the tissue, or in combination with the quantitative predictor described below, or yet further in combination with another image (e.g., overlaid with an anatomical image) or other data relating, for example, to a systemic or local condition of the subject providing a particular clinical context for that subject. Such a condition may comprise a comorbid condition including, for example, hypertension, dyslipidemia, diabetes mellitus, chronic obstructive pulmonary disease, coronary artery disease, chronic kidney disease, or a combination thereof. Furthermore, the coefficient-derived image (e.g., venous coefficient-derived image) may facilitate visualization of a vessel and/or vessel network.

Assessing Based on Heterogeneous Pattern

In some variations, assessing tissue of the subject may comprise assessing a healing status of the wound based on a heterogeneous visual pattern in a single coefficient-derived image 122, where the heterogeneous pattern is indicative of an actual or suspected wound. The heterogeneous pattern may manifest as a result of a difference in the coefficients in the coefficient-derived images, which correlates with a difference in a dynamic behavior of an imaging agent (e.g., ICG, etc.) in the tissue. Such information from a single coefficient-derived image (e.g., venous coefficient-derived image) may facilitate providing a prognosis for the health of the tissue, as the nature of the pattern may provide insight into the healing potential or stage of the actual or suspected wound tissue, without requiring the analysis of multiple image taken over time in order to determine current healing potential.

Figure 5A:
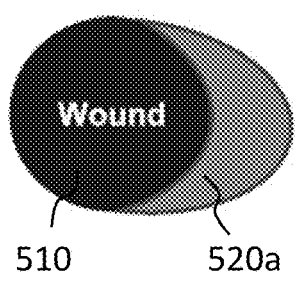
FIGS. 5A-5D illustrate a schematic representation of the wound healing process as depicted in coefficient-derived image maps.
Figure 5B:
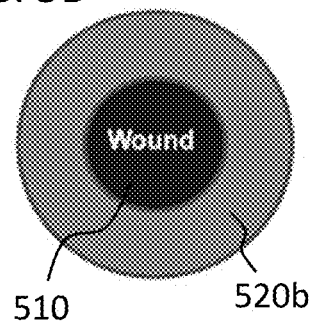
Figure 5C:
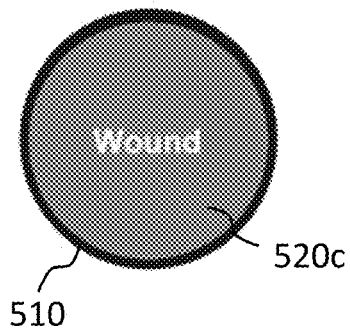
Figure 5D:
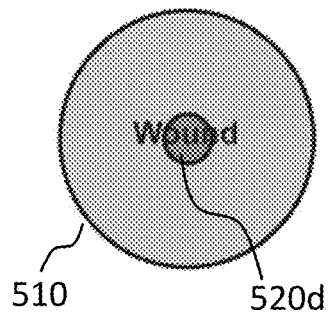

For instance, as further discussed in the examples below, in a healthy organism, the wound healing process manifests itself in a temporal progression of distinct patterns in a coefficient-derived image (e.g., venous coefficient-derived image). By identifying these patterns, one can both assess the severity of the damage in the tissue and predict the healing potential of the tissue (e.g., wound). Various stages of the wound healing process are exemplified in the schematics of FIGS. 5A-5D. An early stage of the healing process may comprise an increased efflux or venous activity inside or around the wound, which is schematically illustrated in FIG. 5A generally as a partial ring or crescent 520a around or embracing the wound 510 (e.g., Stage 1). This pattern 520a is correlated with the highest degree of tissue damage and is the furthest away from healing. As shown in the schematic of FIG. 5B, as the healing progresses, the partial ring transforms into a complete ring pattern 520b surrounding the wound 510 (e.g., Stage 2). The complete ring pattern 520b is still indicative of a severe compromise to the tissue perfusion, but is an improvement in healing status compared to the partial ring pattern 520a illustrated in FIG. 5A. As shown in FIG. 5C, the complete ring pattern transforms into a "filled circle" pattern 520c (e.g., Stage 3) substantially overlaid with the wound 510 as the healing process continues. The "filled circle" pattern 520c appears to be the most common reaction to a relatively minor perfusion compromise and is associated with an active state of healing. As the healing process further continues, the pattern eventually transforms into the "collapsed circle" pattern 520d (e.g., Stage 4) lying within the original wound region 510, as shown in FIG. 5D.

Although a single coefficient-derived image may be sufficient to determine or predict current healing potential, in some variations, the method may further include comparing a plurality of coefficient-derived image maps that are based on a plurality of time series of signal intensity data captured over time, and assessing, for example, progress of healing of tissue, efficacy of clinical intervention, or a combination thereof based on the comparison of the plurality of coefficient-derived image maps.

Assessing Based on a Quantitative Predictor

In some variations, as shown in FIG. 1, assessing tissue of the subject may include generating a quantitative predictor based on at least a portion of the coefficient-derived image 124. For instance, the quantitative predictor may quantify particular characteristics of a single coefficient-derived image, such as area of abnormal activity (e.g., number of pixels or voxels of a region of abnormal activity), eccentricity of abnormal activity (e.g., to indicate how different from a "filled circle" pattern the current pattern is), etc.

In some variations in which the first and second coefficient-derived image maps (e.g., arterial and venous coefficient-derived image maps) have been generated as shown in FIG. 4, assessing tissue of the subject 420 may include generating a quantitative predictor based on the first and second coefficient-derived image maps. Based on the in vivo pre-clinical data (described below in the examples), it appears that the initial increase in efflux venous activity is followed by an increase of the influx arterial activity. In contrast to the range of different patterns exhibited during the healing process and evident in the venous coefficient-derived image map, the arterial coefficient-derived image shows predominantly one pattern during all stages of the wound healing progress, namely the filled circle pattern (similar to FIG. 5C). The area and intensity of the filled circle pattern in the arterial coefficient-derived image map may change from one stage to another, but its shape generally may remain unchanged. It further appears that there is a phase shift between the formation of the influx and efflux patterns. Namely, throughout the healing process, the efflux patterns are first to appear and first to dissipate into a normal pattern, while the influx circle pattern forms some time later in the process, and lingers after the efflux pattern has disappeared. Accordingly, the quantitative predictor of the progress of healing of the tissue may, for example, be based on a comparison of the arterial and venous coefficient image maps and thus serve as an objective characterization of a state or progress of healing of the tissue.

For example, the quantitative predictor may be based on a ratio or other comparative metric of the relative sizes of selected regions in the first and second coefficient-derived image maps. For instance, the area or volume of a region of abnormal activity in the venous coefficient-derived image map can be measured (e.g., number of pixels or voxels) and compared to the measured area of volume of a region of abnormal activity in the arterial coefficient-derived image map (e.g., dividing an area of a first selected region of the venous coefficient-derived image map by the area of a second selected region of the arterial coefficient-derived image map). The quantitative predictor may thus numerically characterize a state or progress of healing. For example, when both venous and arterial areas of increased activity in the respective coefficient-derived images cover about the same parts of tissue in a "filled circle" pattern, a ratiometric quantitative predictor may be equal to about 1, indicating that the wound is in its ongoing process of healing. Furthermore, such a quantitative predictor may additionally or alternatively be used to provide prognostic information of wound healing, such as whether to stop or continue treatment.

Although a single quantitative predictor obtained for a subject at one particular time (e.g., a single clinical session) may be sufficient to determine or predict current healing potential, in some variations, the method may further include tracking a change in the quantitative predictor over time. For instance, a change in the quantitative predictor may be represented in a graph form which facilitates deriving information about the rate and slope. A graphical representation of the quantitative predictor over time may facilitate an evaluation of a change in the quantitative predictor over time, which is indicative, for example, of a change in a state or healing progress of the wound over time.

In some variations, the quantitative predictor may be correlated with a risk estimate for clinically relevant (e.g., perfusion-related) condition. Such assessments may be made pre-intervention, during treatment/procedure, and post-intervention. The method may also further comprise defining a diagnosis to identify and characterize a clinically relevant (e.g., perfusion-related) condition in the subject pre-intervention, during treatment/procedure, and post-intervention. Alternatively, the method may omit such correlation and/or diagnosis.

In various further embodiments, the coefficient values, the coefficient-derived images, and/or the quantitative predictor(s) may be used as input into a machine learning process (i.e., getting a processor or a computer to act without being explicitly programmed), deep machine learning, data mining, and/or pattern recognition where the machine learning is then subsequently used for assessment of a time series of signal intensity data or an image of tissue.

Displaying the Coefficient-Derived Image Map on a Display

In some variations, as shown in FIG. 1, the method may further include displaying one or more coefficient-derived image maps on a display 118. For example, the coefficient-derived image map may be displayed within a user interface on a video monitor in a fluorescence imaging system, or other suitable display. The coefficient-derived image map may be displayed alone, or in combination with another image (e.g., overlaid with or superimposed on an anatomical image) or other data. Such other data may relate, for example, to a systemic or local condition of the subject providing a particular clinical context for that subject. Such a condition may comprise a comorbid condition including, for example, hypertension, dyslipidemia, diabetes mellitus, chronic obstructive pulmonary disease, coronary artery disease, chronic kidney disease, or a combination thereof. Furthermore, the coefficient-derived image map may additionally or alternatively be displayed in combination with the quantitative predictor described above. In some variations, the coefficient-derived image map may be displayed with a ranking map image and/or a wound index value characterizing a wound in the tissue such as those described in U.S. patent application Ser. No. 15/013,945, filed Feb. 2, 2016 and entitled "METHODS AND SYSTEMS FOR CHARACTERIZING TISSUE OF A SUBJECT," which is hereby incorporated in its entirety by this reference.

Systems for Assessing Healing of Tissue

A system for assessing healing of tissue includes one or more processors and memory having instructions stored thereon, wherein the instructions when executed by the one or more processors cause the system to perform the methods substantially as described above for assessing healing of tissue.

Figure 6:
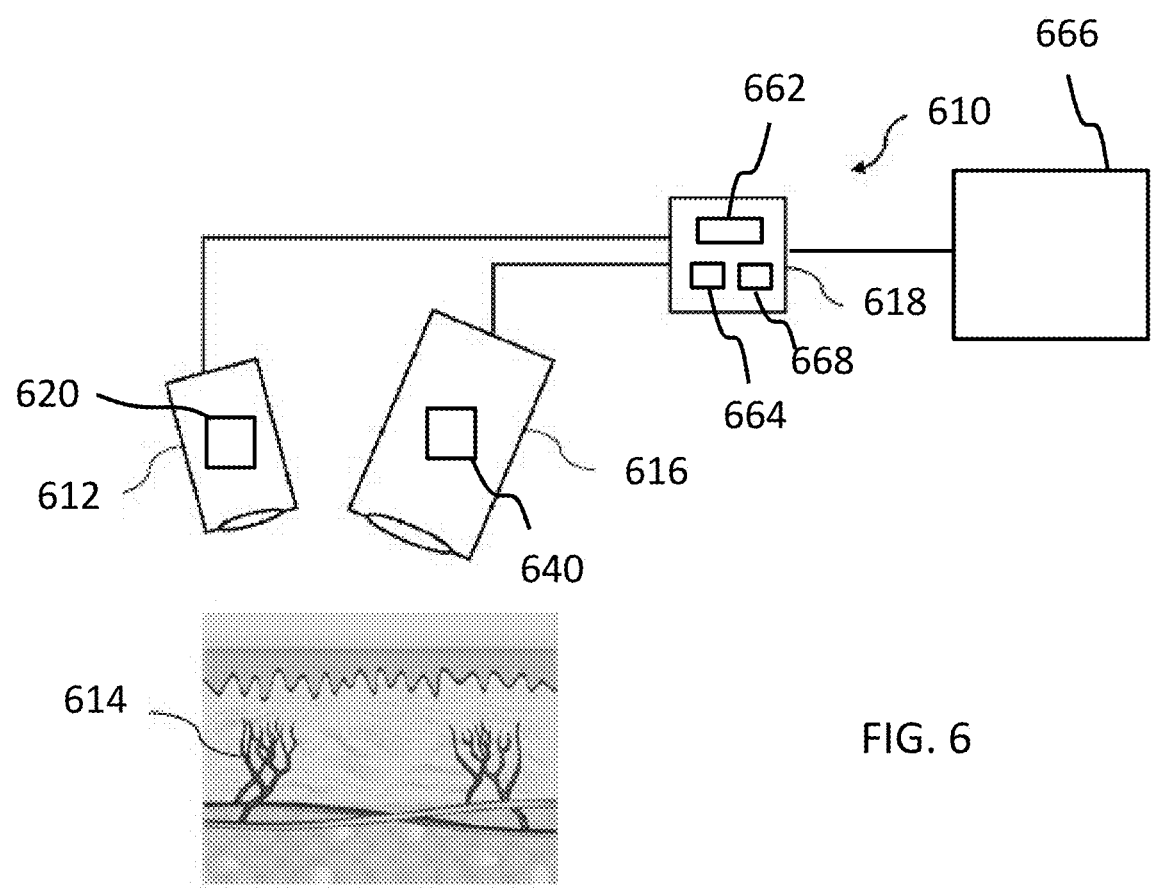
FIG. 6 is an illustrative depiction of an exemplary fluorescence imaging system configured to assess healing of tissue of a subject.

In some variations, the system for characterizing tissue of a subject is a fluorescence imaging system. FIG. 6 is a schematic example of a fluorescence imaging system 610. The fluorescence imaging system 610 comprises a light source 612 to illuminate the tissue of the subject to induce fluorescence emission from a fluorescence imaging agent 614 in the tissue of the subject (e.g., in blood), an image acquisition assembly 616 configured to generate the time series of fluorescence signal intensity data from the fluorescence emission, and a processor assembly 618 configured to process the generated time series of signal intensity data according to any of the variations of the methods described herein. The processor assembly 618 may include memory 668 with instructions thereon, a processor module 662 configured to execute the instructions on memory 668 to process the time series of signal intensity data as described in connection with the various embodiments of the methods described above, and a data storage module 664 to store the unprocessed and/or processed time series of signal intensity data. In some variations, the memory 668 and data storage module 664 may be embodied in the same storage medium, while in other variations the memory 668 and the data storage module 664 may be embodied in different storage mediums. The system may further include a display 666 on which to display images and other data, such as some or all of the time series of fluorescence images representing the signal intensity data or other input data, a quantitative predictor, a ranking map image, and/or a wound index value.

Figure 7:
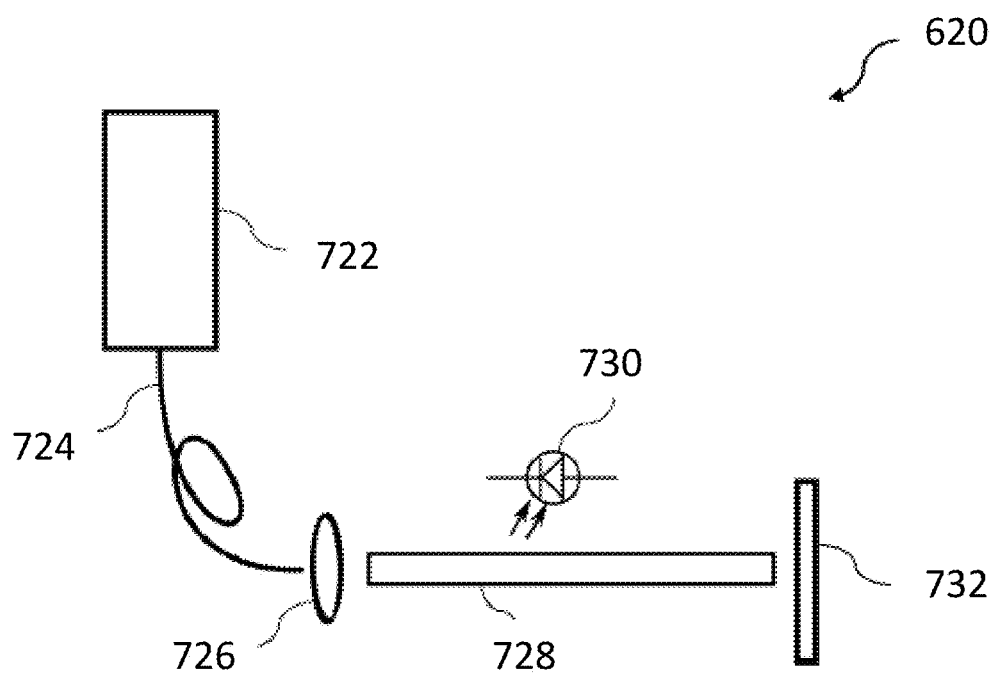
FIG. 7 is an illustrative depiction of an exemplary illumination module of a fluorescence imaging system configured to assess healing of tissue of a subject.

In some variations, the light source 612 includes, for example, an illumination module 620. Illumination module 620 may include a fluorescence excitation source configured to generate an excitation light having a suitable intensity and a suitable wavelength for exciting the fluorescence imaging agent 614. As shown in FIG. 7, the illumination module 620 may comprise a laser diode 722 (e.g., which may comprise, for example, one or more fiber-coupled diode lasers) configured to provide an excitation light to excite the fluorescence imaging agent (not shown) in tissue of the subject. Examples of other sources of the excitation light which may be used in various embodiments include one or more LEDs, arc lamps, or other illuminant technologies of sufficient intensity and appropriate wavelength to excite the fluorescence imaging agent in the tissue. For example, excitation of the fluorescence imaging agent in blood, wherein the fluorescence imaging agent is a fluorescence dye with near infra-red excitation and emission characteristics, may be performed using one or more 793 nm, conduction-cooled, single bar, fiber-coupled laser diode modules from DILAS Diode Laser Co, Germany.

Referring again to FIG. 6, in some variations, the light output from the light source 612 may be projected through one or more optical elements to shape and guide the output being used to illuminate the tissue area of interest. The optical elements may include one or more lenses, light guides, and/or diffractive elements so as to ensure a flat field over substantially the entire field of view of the image acquisition assembly 616. The fluorescence excitation source may be selected to emit at a wavelength close to the absorption maximum of the fluorescence imaging agent 614 (e.g., ICG, etc.). For example, as shown in FIG. 7, the output 724 from the laser diode 722 may be passed through one or more focusing lenses 726, and then through a homogenizing light pipe 728 such as, for example, light pipes commonly available from Newport Corporation, USA. Finally, the light may be passed through an optical diffractive element 732 (i.e., one or more optical diffusers) such as, for example, ground glass diffractive elements also available from Newport Corporation, USA. Power to the laser diode 722 may be provided by, for example, a high-current laser driver such as those available from Lumina Power Inc. USA. The laser may optionally be operated in a pulsed mode during the image acquisition process. An optical sensor such as a solid state photodiode 730 may be incorporated into the illumination module 620 and may sample the illumination intensity produced by the illumination module 620 via scattered or diffuse reflections from the various optical elements. In some variations, additional illumination sources may be used to provide guidance when aligning and positioning the module over the area of interest.

Figure 8:
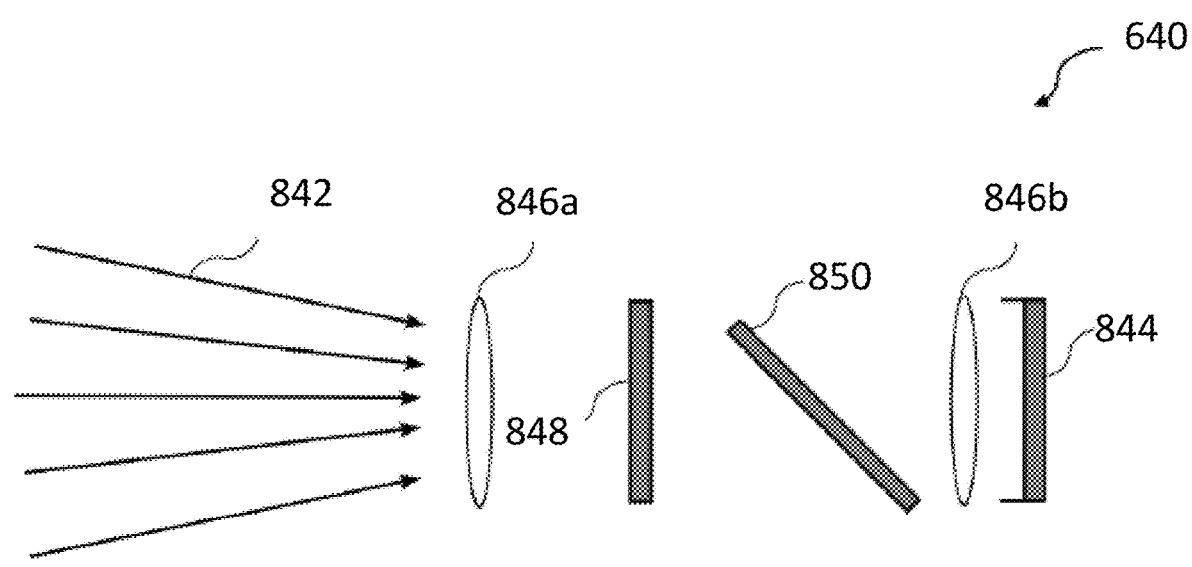
FIG. 8 is an exemplary camera module of a fluorescence imaging system configured to assess healing of tissue of a subject.
Figure 9A:
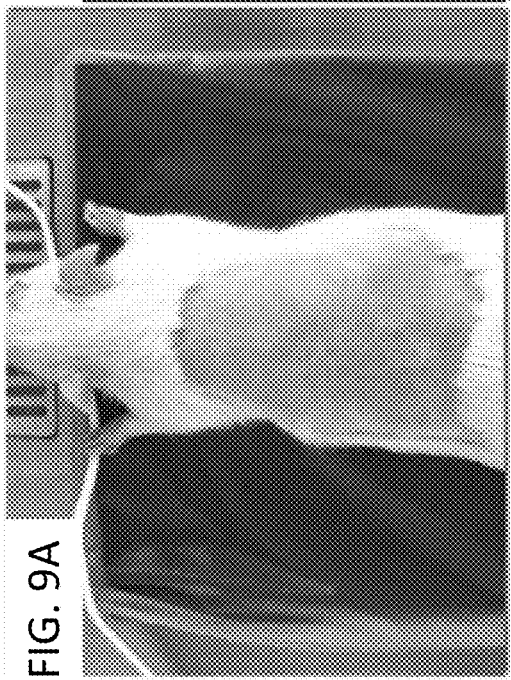
FIGS. 9A-9D depict results for the control rat 24 hours after removal of pressure magnets.
Figure 9B:
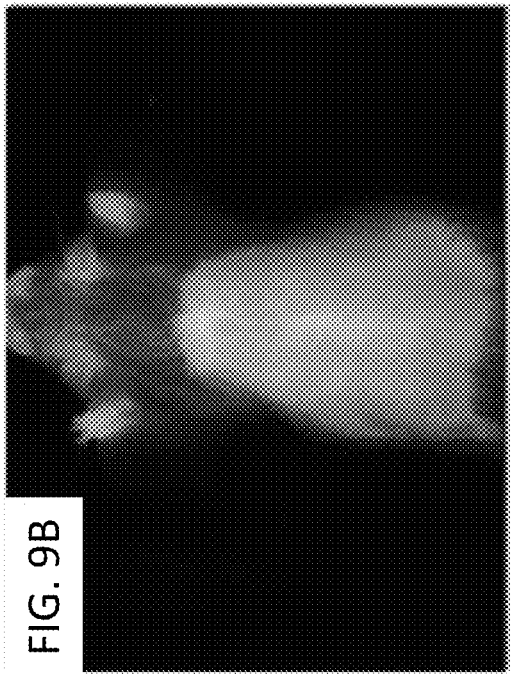
Figure 9C:
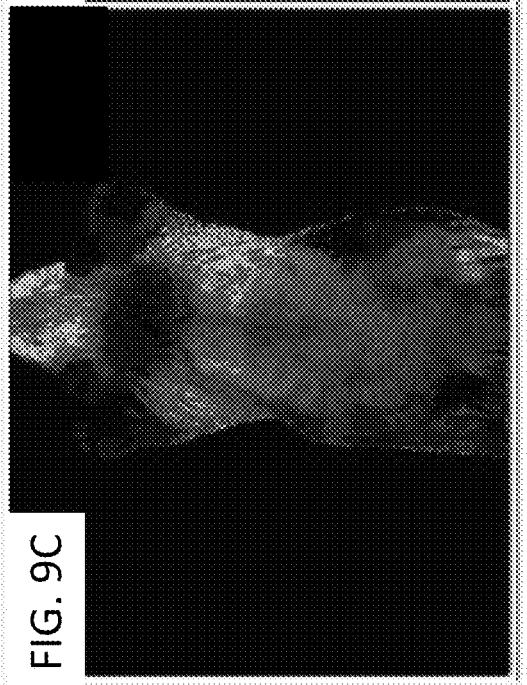
Figure 9D:
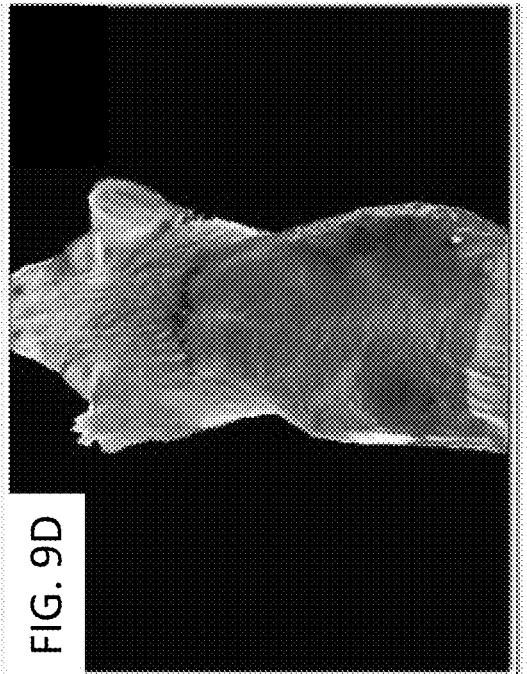

Referring again to FIG. 6, in some variations, the image acquisition assembly 616 may be a component of a fluorescence imaging system 610 configured to acquire the time series of signal intensity data from the fluorescence emission from the fluorescence imaging agent 614. The image acquisition assembly 616 may include a camera module 640. As shown in FIG. 8, the camera module 640 may acquire images of the fluorescence emission 842 from the fluorescence imaging agent in the tissue by using a system of imaging optics (e.g., 846a, 846b, 848 and 850) to collect and focus the fluorescence emission onto an image sensor assembly 844. The image sensor assembly 844 may comprise at least one 2D solid state image sensor. The solid state image sensor may be a charge coupled device (CCD), a CMOS sensor, a CID or similar 2D sensor technology. The charge that results from the optical signal transduced by the image sensor assembly 844 is converted to an electrical video signal, which includes both digital and analog video signals, by the appropriate read-out and amplification electronics in the camera module 640.

According to an exemplary embodiment of a fluorescent imaging system, the light source may provide an excitation wavelength of about 800 nm+/−10 nm, and the image acquisition assembly uses emission wavelengths of at least 820 nm with NIR-compatible optics for, for example, ICG fluorescence imaging. In an exemplary embodiment, the NIR-compatible optics may include a CCD monochrome image sensor having a GigE standard interface and a lens that is compatible with the sensor with respect to optical format and mount format (e.g., C/CS mount).

In some variations, the processor module 662 comprises any computer or computing means such as, for example, a tablet, laptop, desktop, networked computer, or dedicated standalone microprocessor. For instance, the processor module 662 may include one or more central processing units (CPU). In an exemplary embodiment, the processor module 662 is a quad-core, 2.5 GHz processor with four CPUs where each CPU is a microprocessor such as a 64-bit microprocessor (e.g., marketed as INTEL Core i3, i5, or i7, or in the AMD Core FX series). However, in other embodiments, the processor module 662 may be any suitable processor with any suitable number of CPUs and/or other suitable clock speed.

Inputs for the processor module 662 may be taken, for example, from the image sensor 844 of the camera module 640 shown in FIG. 8, from the solid state photodiode 730 in the illumination module 620 in FIG. 7, and/or from any external control hardware such as a footswitch or remote-control. Output is provided to the laser diode driver and optical alignment aids. As shown in FIG. 6, in some variations, the processor assembly 618 may have a data storage module 664 with the capability to save the time series of images, or data representative thereof, or other input data to a tangible non-transitory computer readable medium such as, for example, internal memory (e.g. a hard disk or flash memory), so as to enable recording and processing of acquired data. In some variations, the processor module 662 may have an internal clock to enable control of the various elements and ensure correct timing of illumination and sensor shutters. In some variations, the processor module 662 may also provide user input and graphical display of outputs. The fluorescence imaging system may optionally be configured with a video display 666 or other monitor to display the time series of fluorescence images as they are being acquired or played back after recording. The video display 666 may additionally or alternatively visualize data generated during performance of the methods described herein, such as a coefficient-derived image map, quantitative predictor, ranking map image and/or wound index value.

In operation of the exemplary system described in FIGS. 6-8, the subject is positioned relative to fluorescence imaging system 610 such that an area of interest (e.g., target tissue region) is located beneath the light source 612 and the image acquisition assembly 616 such that the illumination module 620 of light source 612 produces a substantially uniform field of illumination across substantially the entire area of interest. In some variations, prior to the administration of the fluorescence imaging agent 614 to the subject, an image may be acquired of the area of interest for the purposes of background deduction. To acquire fluorescence images, the operator of the fluorescence imaging system 610 may initiate the acquisition of the time series of fluorescence images by depressing a remote switch or foot-control, or via a keyboard (not shown) connected to the processor assembly 618. As a result, the light source 612 is turned on and the processor assembly 618 begins recording the fluorescence image data provided by the image acquisition assembly 616. When operating in the pulsed mode of the embodiment, the image sensor 844 in the camera module 640 is synchronized to collect fluorescence emission following the laser pulse produced by the diode laser 722 in the illumination module 620. In this way, maximum fluorescence emission intensity is recorded, and signal-to-noise ratio is optimized. In this embodiment, the fluorescence imaging agent 614 is administered to the subject and delivered to the area of interest via arterial flow. Acquisition of the time series of fluorescence images is initiated, for example, shortly after administration of the fluorescence imaging agent 614, and the time series of fluorescence images from substantially the entire area of interest is acquired throughout the ingress of the fluorescence imaging agent 614. The fluorescence emission from the region of interest is collected by the collection optics of the camera module 640. Residual ambient and reflected excitation light is attenuated by subsequent optical elements (e.g., optical element 850 in FIG. 8 which may be a filter) in the camera module 640 so that the fluorescence emission can be acquired by the image sensor assembly 844 with minimal interference by light from other sources.

In some variations, following the acquisition or generation of the time series of fluorescence images, the processor assembly 618 (e.g., processor module 662 or other processor) may then be initiated to execute instructions stored on memory 668 and perform one or more methods as described herein. The system 610 may visualize on display 666 the ranking map and/or any clinical correlations or diagnosis derived therefrom or both may be displayed to the user as, for example, a grayscale or false color image, and/or stored for subsequent use. Additionally or alternatively, the system 610 may display on display 666 a quantitative predictor.

In some variations, the system for assessing healing of tissue comprises a user interface, a processor configured to communicate with the user interface, and a non-transitory computer-readable storage medium having instructions stored which, when executed by the processor, cause the processor to perform one or more of the methods for assessing healing of tissue described herein. In some variations, the processor may be a component of the imaging system. In other variations, the processor may be located remotely from and in communication with an imaging system, where the imaging system may be the fluorescence imaging system described above, or any suitable imaging system.

A tangible non-transitory computer readable medium having computer-executable (readable) program code embedded thereon may provide instructions for causing one or more processors to, when executing the instructions, perform one or more of the methods for assessing healing of tissue described herein. Program code can be written in any appropriate programming language and delivered to the processor in many forms, including, for example, but not limited to information permanently stored on non-writeable storage media (e.g., read-only memory devices such as ROMs, CD-ROM disks, etc.), information alterably stored on writeable storage media (e.g., hard drives or the like), information conveyed to the processor through communication media, such as a local area network, a public network such as the Internet, or any type of media suitable for storing electronic instruction. When carrying computer readable instructions that implement the various embodiments of the method of the present invention, such computer readable media represent examples of various embodiments of the present invention. In various embodiments, the tangible non-transitory computer readable medium comprises all computer-readable media, and the present invention scope is limited to computer readable media wherein the media is both tangible and non-transitory.

A kit may include any part of the systems described herein and the fluorescence imaging agent such as, for example, a fluorescence dye such as ICG or any suitable fluorescence imaging agent. In further aspects, a kit may include a tangible non-transitory computer readable medium having computer-executable (readable) program code embedded thereon that may provide instructions for causing one or more processors, when executing the instructions, to perform one or more of the methods for assessing healing of tissue described herein. The kit may include instructions for use of at least some of its components (e.g., for using the fluorescence imaging agent, for installing the computer-executable (readable) program code with instructions embedded thereon, etc.). In yet further aspects, there is provided a fluorescence imaging agent such as, for example, a fluorescence dye for use in in the methods and systems described herein.

EXAMPLES

In some of the examples described below, "color image" refers to an image obtained under ambient lighting conditions. Additionally, "maximum perfusion image" refers to a map created by assigning each pixel in the calculation region of the time series of signal intensity data the value of its maximum intensity reached during the entire measurement period. Furthermore, "arterial coefficient-derived image" and "venous coefficient-derived image" refer to an image generated from $C_{Inf}$ coefficients and $C_{Eff}$, respectively, using the exemplary model of Formula 1 described above.

A. Pre-Clinical In Vivo Data—Pressure-Induced Wound Experimental Protocol

The protocol to induce the formation of pressure-induced wounds in rodents has been described in Stadler I, Zhang R Y, Oskoui P, Whittaker M S, Lanzafame R J, Development of a simple, noninvasive, clinically relevant model of pressure ulcers in the mouse, J. Invest. Sung. 2004 July-August, 17(4): 221-227, and Nunan R, Harding K G, Martin P, Clinical Challenges of Chronic Wounds: Searching for an Optimal Animal Model to Recapitulate their Complexity, *Disease Models & Mechanisms* (2014) 7, 1205-1213.

White Wistar Rats (n=10) were anesthetized with about 2-4% isoflurane and the dorsal hair was removed. The dorsal skin of the back over the shoulder blades was gently pulled and placed between two disc-shaped magnetic plates (5 mm diameter, 2.4 g weight), which created a 5 mm skinfold between the magnets. Magnets remained in position to induce the wound for about 1.0 h for 3 days in an animal group consisting of 3 animals, and about 3.0 h for 3 days in an animal group consisting of 5 animals. This procedure was used to induce ischemic areas of variable severity. Animals remained anesthetized during this time. Isoflurane was turned down to the lowest concentration that still rendered the animal unconscious (about 1-2%). If respiratory depression was noted (i.e., respirations lower than 50-60 per minute, gasping, decreased depth of respirations, expired $CO_2$ increasing), then the animals were intubated and ventilated using a Harvard rodent-specific ventilator for the duration of the procedure. Animals were given all the supportive care required for the anesthetic session including: heat (animals were kept on a circulating hot water blanket with temperature maintained above 35° C., fluids (animals were given 5 ml of warmed Lactated Ringers Solution (LRS) subcutaneously before and after the procedure), pain medications (animals were given an injection of ketoprofen at 5 mg/kg prior to the procedure), and (D) eye lubrication (animals' eyes were protected throughout the procedure with Lacrilube®). Animals were recovered in a heated clean cage until ambulatory. Monitoring commenced for the remainder of the afternoon and evening to ensure signs of pain or irritation were not noted. Ketoprofen at the dose above was given at least one more time at 24 h post-procedure. Assessment of blood perfusion in tissue and visual inspection of the ischemic regions were performed at about 3 hours, 24 hours, and 48 hours after the removal of the magnetic plates.

Example 1—No Wound

Results were obtained for a control animal that did not develop any wound after removal of the magnetic plates described above. FIGS. 9A-9D illustrate results for the control animal after 24 hours following removal of the magnetic plates, while FIGS. 10A-10D illustrate results for the control animal after 48 hours following removal of the magnetic plates. The color images (FIGS. 9A and 10A), maximum intensity images (FIGS. 9B and 10B), arterial coefficient-derived images (FIGS. 9C and 10C), and venous coefficient-derived images (FIGS. 9D and 10D) do not depict any visible abnormalities.

Example 2—Minor Pressure-Induced Wound

Results were obtained for an animal with a minor pressure-induced wound resulting from application of the magnetic plates described above. The results in FIGS. 11-13 illustrate the healing progression of the minor pressure-induced wound, which healed almost completely without intervention after about 48 h, as depicted in a series of color images, maximum perfusion images, arterial coefficient-derived images, and venous coefficient-derived images. In particular, FIGS. 11A-11D illustrate results for the animal with the minor wound after 3 hours following removal of the magnetic plates, FIGS. 12A-12D illustrate results for the animal with the minor wound after 24 hours following removal of the magnetic plates, and FIGS. 13A-13D illustrate results for the animal with the minor wound after 48 hours following removal of the magnetic plates.

After 3 hours, as shown in the color image of FIG. 11A, visible redness on the skin surface of the animal can be seen. This visible redness corresponds to increased activity in the maximum perfusion image (FIG. 11B), the arterial coefficient-derived image (FIG. 11C), and venous coefficient-derived image (FIG. 11D). Furthermore, the venous coefficient-derived image of FIG. 11D shows a "filled circles" pattern of abnormally high activity. The arterial coefficient-derived image of FIG. 11C also demonstrates increased activity in the wounded tissue, but the pattern is still in its early stages of formation (scattered high-activity area, as contrasted with the smoothly "filled" circles of the venous coefficient-derived image of FIG. 11D).

After 24 hours, as shown in the color image of FIG. 12A, moderate decrease in the area of visible skin redness is apparent, which again corresponds to increased activity in the maximum perfusion image (FIG. 12B), the arterial coefficient-derived image (FIG. 12C), and venous coefficient-derived image (FIG. 12D). Moreover, the venous coefficient-derived image of FIG. 12D continues to show a "filled circles" pattern, but the pattern of highest activity now appears to be concentrated toward the center of the wound and the area of the abnormal venous activity has decreased as well. The arterial coefficient-derived image of FIG. 12C shows high activity covering each wound circle.

After 48 hours, almost no abnormalities are apparent in the color image (FIG. 13A), maximum perfusion image (FIG. 13B), arterial coefficient-derived image (FIG. 13C), and venous coefficient-derived image (FIG. 13D). Although some increased activity is shown in the arterial coefficient-derived image of FIG. 13C (as shown by the arrow), the wounds are on the verge of being fully healed.

Example 3—Severe Pressure-Induced Wound

Results were obtained for an animal with a severe pressure-induced wound resulting from application of the magnetic plates described above. The results in FIGS. 14-19 illustrate the healing progression of the severe pressure-induced wound as depicted in a series of color images, maximum perfusion images, arterial coefficient-derived images, and venous coefficient-derived images. In particular, FIGS. 14A-14D illustrate results for the animal with the severe wound immediately following removal of the magnetic plates, FIGS. 15A-15D illustrate results for the animal with the severe wound after 2 hours following removal of the magnetic plates, FIGS. 16A-16D illustrate results for the animal with the severe wound after 24 hours following removal of the magnetic plates, FIGS. 17A-17D illustrate results for the animal with the severe wound after 48 hours following removal of the magnetic plates, FIGS. 18A-18D illustrate results for the animal with the severe wound after 72 hours following removal of the magnetic plates, and FIGS. 19A-19D illustrate results for the animal with the severe wound after 8 days following removal of the magnetic plates.

Immediately after the removal of the magnetic plates, as shown in the color image of FIG. 14A, deep, red indentations are visible on the surface of the skin. Additionally, there is a total absence of both arterial and venous activity in the wounds, as evidenced by the appearance of the arterial coefficient-derived image (FIG. 14C) and venous coefficient-derived image (FIG. 14D) which show black area generally corresponding to the pressure circles. This abnormal absence of arterial and venous activity is not visible from the maximum perfusion image alone (FIG. 14B).

After 2 hours, as shown in the color image of FIG. 15A, reduced redness on the affected areas of the skin surface of the animal can be seen. Arterial influx into the wounds is still almost non-existent, as indicated by the black regions generally corresponding to the pressure wound as shown in the arterial coefficient-derived image of FIG. 15C. However, there is increased venous activity around the center of the wounds, as shown in the venous coefficient-derived image of FIG. 15D. As earlier, the maximum perfusion image (FIG. 15B) failed to show any abnormality. Note that a significant difference between the efflux venous pattern in the severe wound example (FIG. 15D) and the efflux venous pattern in the minor wound example (FIG. 12D) is that the severe wound example exhibits a partial "halo pattern" around the wounds while the minor wound example exhibits a "filled circle" pattern around the wounds.

After 24 hours, as shown in the color image of FIG. 16A, only minor abnormalities in skin color of the animal are externally visible. These minor skin discolorations are accompanied by dramatically increased arterial and venous activity around the wounds, as shown in the arterial coefficient-derived image (FIG. 16C) and venous coefficient-derived image (FIG. 16D). However, again, no abnormalities are detectable in the maximum perfusion image (FIG. 16B). Furthermore, the efflux pattern of venous activity in FIG. 16D now forms a complete ring enclosing around each of the wounds.

After 48 hours, as shown in the color image of FIG. 17A, only minor abnormalities still remain in the skin color of the animal. Some increased arterial activity around the wounds is apparent in the arterial coefficient-derived image (FIG. 17C). The efflux pattern of venous activity in the venous coefficient-derived image (FIG. 17D) has transformed into the "filled circle" pattern similar to that observed during the early stages of the minor wound example (e.g., FIG. 11C). However, only minor abnormalities are detectable in the maximum perfusion image (FIG. 17B).

After 72 hours, there is a noticeable decline in the visual appearance of the skin surface of the animal as shown in the color image of FIG. 18A, accompanied by extreme influx arterial activity as shown in the arterial coefficient-derived image of FIG. 18C. In contrast, as shown in the venous coefficient-derived image of FIG. 18D, efflux venous activity has decreased in both the size and intensity of the abnormal areas, and there is convergence of efflux venous activity toward the center one of the wounds (the wound on the righthand side of the image). Again, only minor abnormalities are detectable in the maximum perfusion image (FIG. 18B).

After 8 days, as shown in the color image of FIG. 19A, a significant improvement in the appearance of the skin surface of the animal is apparent. There is still an increase in influx arterial activity in the affected tissue as shown in the arterial coefficient-derived image of FIG. 19C, while the venous activity pattern shown in the venous coefficient-derived image of FIG. 19D has almost collapsed into a small bright region in the center of the wound.

B. Clinical Data—Application to Wound Management

Observations from the in vivo pre-clinical data were evaluated and applied in the context of assessing chronic wounds in human subjects. A single, individual coefficient-derived image provides an indication of a state of the wound (e.g., severity, activity of the wound) and can be used alone or in combination with qualitative visualization to facilitate, for example, an enhanced diagnosis and to assess the effectiveness of any care strategies.

Example 4—Severe Non-Healing Shin Ulcer (Stage 1 of Wound Healing Presenting a Partial Ring Pattern)

As shown in FIGS. 18A-18C, exemplary results were generated relating to an application of the methods and systems described herein to assess tissue of a subject, particularly for wound management of a severe non-healing shin ulcer. The color image in FIG. 20A shows a wound externally observed during an assessment of the patient by a clinician. Maximum perfusion images of the wound were generated (not shown) using LUNA® fluorescence imaging system (available from NOVADAQ® Technologies Inc.) and ICG as the fluorescence imaging agent. The arterial coefficient-derived image of FIG. 20B and the venous coefficient-derived image of FIG. 20C show the wound pattern with respect to influx arterial activity and efflux venous activity, respectively. The patterns shown in FIGS. 20B and 20C are consistent with the indicators of the partial ring efflux pattern observed in connection with the pre-clinical in vivo experiments discussed above. As was discussed above, this pattern is correlated with the highest degree of tissue damage and is the farthest away from healing, which is apparent in this clinical case. As is shown in FIG. 20A, redness appears on the affected areas of the skin. A clinician looking at FIG. 20A alone would get some visual indication that the wound is severe, but it would not be clear from this visual assessment whether this is a non-healing wound or whether it has the potential to heal. However, the venous coefficient-derived image in FIG. 20C shows a partial ring adjacent the wound forming a halo adjacent the wound, which is indicative of increased venous activity and aids the clinician in clearly classifying the wound as having highly damaged tissue and being far from healing.

Example 5—Traumatic Fracture Wound (Stage 2 of Wound Healing Presenting a Complete Ring Pattern)

As shown in FIGS. 21A-21C, exemplary results were generated relating to an application of the methods and systems described herein to assess tissue of a subject, particularly for wound management of a traumatic fracture wound. The patient was a 72-year-old male who incurred a traumatic, compound bimalleolar fracture of his left ankle that required operative repair with an open reduction/internal-fixation procedure. The surgical site has become fully disrupted, threatening the fixation plates and hence the extremity. Hyperbaric oxygen therapy (HBOT) therapy was recommended. The color image in FIG. 21A shows a wound observed during an initial assessment of the patient with the clinician prior to any therapy applied to the wound. Maximum perfusion images of the wound were generated (not shown) using LUNA® fluorescence imaging system (available from NOVADAQ® Technologies Inc.) and ICG as the fluorescence imaging agent. The arterial coefficient-derived image of FIG. 21B and the venous coefficient-derived image of FIG. 21C show the wound pattern with respect to influx arterial activity and efflux venous activity, respectively. The patterns shown in FIGS. 21B and 21C are consistent with the indicators of the complete ring pattern observed in connection with the pre-clinical in vivo experiments discussed above. As was discussed above, this complete ring pattern is correlated with a severe compromise to the tissue perfusion but with the potential to heal with time, in contrast with the partial ring pattern exhibited by the severe wound discussed in Example 4.

Example 6—Ischemic Wound (Stage 3 of Wound Healing Presenting a Filled Circle Pattern)

Figure 22B:
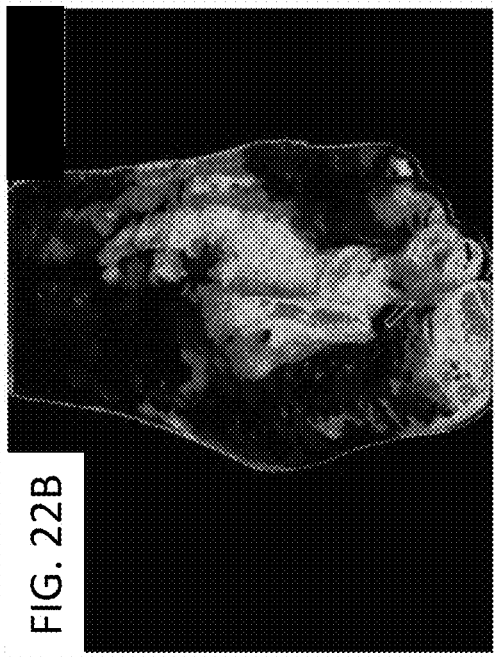
FIGS. 22A-22C depict a color image, an arterial coefficient-derived image, and a venous coefficient-derived image, respectively, for an ischemic wound, where the images are generated according to an exemplary embodiment relating to an application of the methods and systems to assess healing of tissue.
Figure 22C:
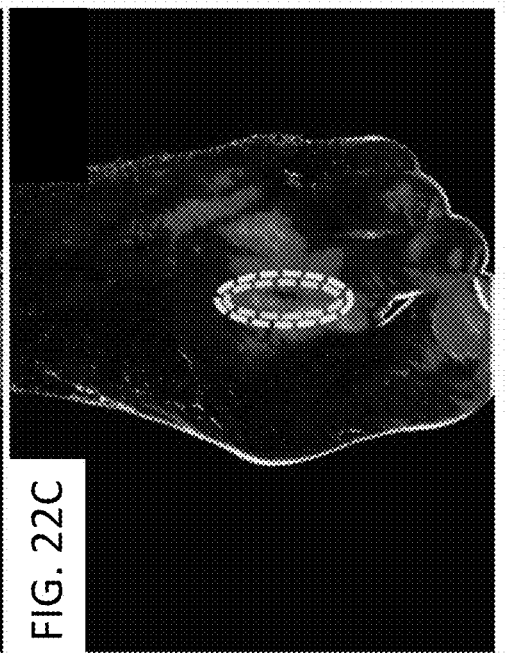
Figure 22A:
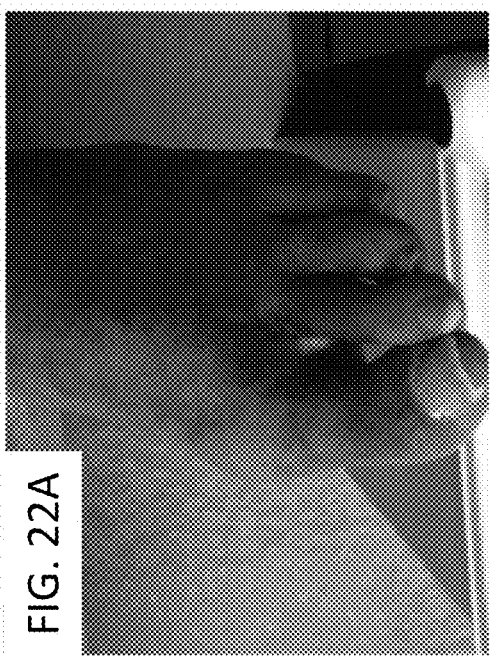

As shown in FIGS. 22A-22C, exemplary results were generated relating to an application of the methods and systems described herein to assess tissue of a subject, particularly for wound management of an ischemic wound. The patient was 51-year-old male with a left foot ischemic wound with an amputated metatarsal with osteomyelitis and ascending fasciitis, and obliterative end arteritis. Refractory to aggressive topical care and antibiotics treatments were applied. HBOT was recommended and started. FIG. 22A is a color image of the wound during an initial assessment and FIGS. 22B and 22C are the corresponding arterial and venous coefficient-derived images respectively. As illustrated in the venous coefficient-derived image in FIG. 22C, the efflux ring is substantially closed to form the "filled circle" pattern, which is observed in relatively minor perfusion compromise and indicates that the wound is in an active state of healing.

Example 7—Ischemic Wound (Stage 4 of Wound Healing Presenting a Collapsed Circle Pattern)

Figure 23A:
FIGS. 23A-23C depict a color image, an arterial coefficient-derived image, and a venous coefficient-derived image, respectively, for an ischemic wound, where the images are generated according to an exemplary embodiment relating to an application of the methods and systems to assess healing of tissue.
Figure 23B:
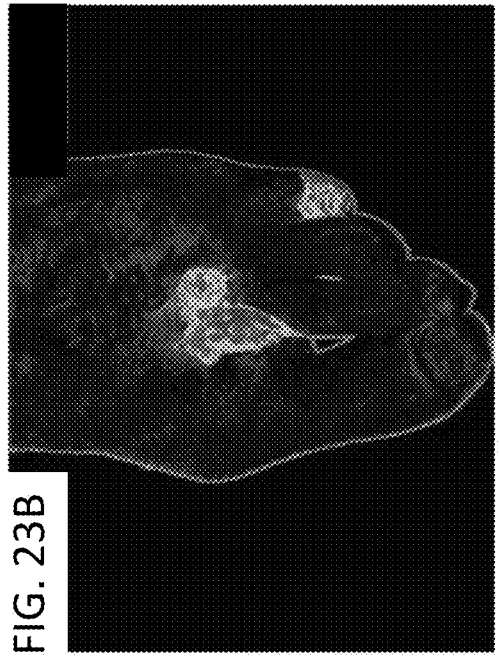
Figure 23C:

As shown in FIGS. 23A-23B, exemplary results were generated relating to an application of the methods and systems described herein to assess tissue of a subject, particularly for follow-up wound management of the ischemic wound in Example 6. The color image (FIG. 23A), arterial coefficient-derived image (FIG. 23B), and venous coefficient-derived image (FIG. 23C) were generated for the patient in Example 6 one month after the same for Example 6 were generated. It is evident from FIG. 23C that the venous activity has almost returned to the normal pattern of tissue that is in its final stages of healing or is healed with uncompromised perfusion, which would not have been apparent from the color image in FIG. 23A.

C. Clinical Data—Application to Plastic and Reconstructive Surgery

Example 8—Mastectomy (Predictability of Necrotic Tissue Based on Coefficient-Derived Images)

As shown in FIGS. 24A-24D, exemplary results were generated relating to an application of the methods and systems described herein to assess tissue of a subject in plastic and reconstructive breast surgery procedures. Data was collected prior to and following a mastectomy performed on a patient. In particular, a pre-incision maximum perfusion image (FIG. 24A) of the tissue was generated using SPY® Elite fluorescence imaging system (available from NOVADAQ® Technologies Inc.), where ICG was used as the fluorescence imaging agent. FIGS. 24B and 24C are the corresponding arterial and venous coefficient-derived images respectively. The pre-incision, coefficient-derived images of FIGS. 24B and 24C predictively indicates that tissue in region 2410 of the breast appears to be compromise prior to surgery. However, the corresponding pre-incision, maximum perfusion image of FIG. 24A fails to enable such a prediction in tissue compromise.

FIG. 24D shows a color image of the breast one month post-reconstruction, with a necrotic tissue region that developed generally in the region 2410 that was previously identified using the coefficient-derived images as being compromised. Thus, the predictive information provided by the coefficient-derived data could have been used to guide the surgical strategy in this case to minimize post-surgical complications.

D. Clinical Data—Application to Visualization of a Vessel Network

Example 9—Vessels in Skin

Figure 25:
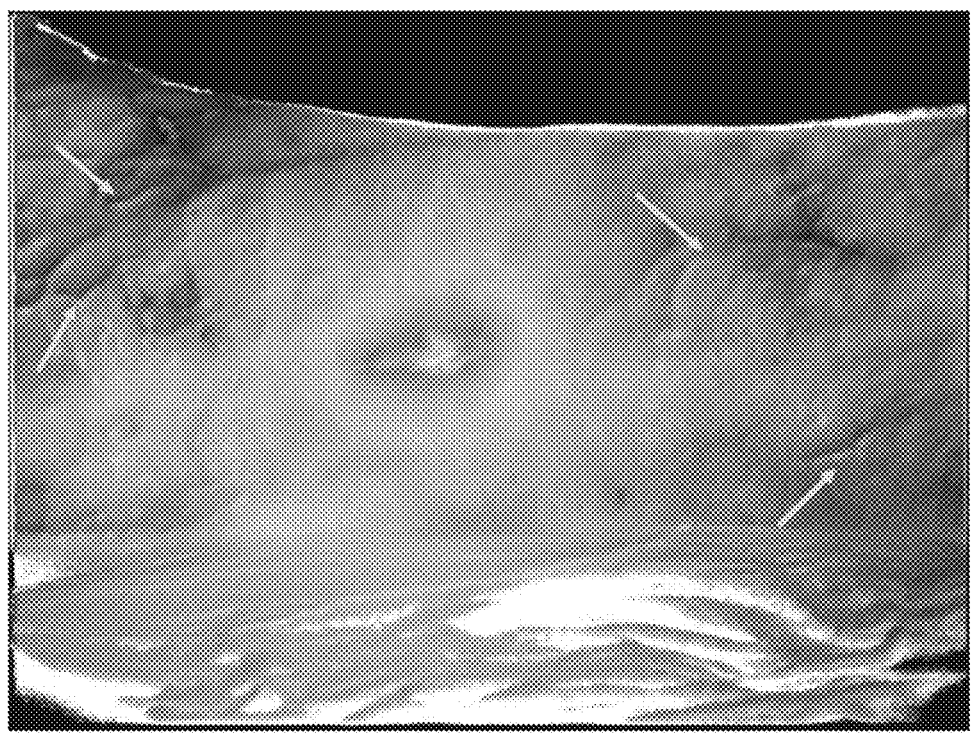
FIG. 25 illustrates a venous coefficient-derived image generated according to an exemplary embodiment relating to an application of the methods and systems to identify a vessel or network of vessels in the skin.

As shown in FIG. 25, exemplary results were generated relating to an application of the methods and systems described herein to assess tissue of a subject in visualization of a vessel network in skin. The patient (same as in Example 5) was a 72-year-old male who incurred a traumatic, compound bimalleolar fracture of his left ankle that required operative repair with an open reduction/internal-fixation procedure. The surgical site has become fully disrupted, threatening the fixation plates and hence the extremity. The venous coefficient-derived image of FIG. 25 visualizes a network of vessels (indicated by arrows) in the skin.

Example 10—Vessel Network in a Foot

FIGS. 26A and 26B illustrate exemplary clinical results generated relating to an application of the methods and systems described herein to identify a vessel network and discriminate between different kinds of vessels in the network. In particular, FIG. 26A is a maximum perfusion image of a healthy foot of a subject. Although tissue perfusion in this image is generally visible, there is limited detail in connection with the vessel network. In contrast, FIG. 26B, which is the corresponding venous coefficient-derived image, provides not only a more detailed visualization of the vessel network but also discriminates between different kinds of vessels as is illustrated by different brightness levels of the vessels in the image (indicated by arrows).

OTHER VARIATIONS

Generally, in one variation, a computer-implemented method of assessing a tissue of a subject includes providing a mathematical model approximating a signal intensity arising from an imaging agent circulating with blood and transiting vasculature of the tissue as a function of time; calculating a coefficient for the mathematical model at one or more points on the tissue using empirical signal intensity data for the imaging agent in the tissue, the empirical signal intensity data comprising a set of intensity values over time; and generating a coefficient-derived image of the tissue from a plurality of the coefficients, wherein a difference in the coefficients correlates with a difference in dynamics of the imaging agent in the tissue. The difference in the coefficients may comprise a difference in a visual pattern in the coefficient-derived image, and the signal intensity resulting from the transit of the imaging agent through vasculature of the tissue may be represented by a time-intensity curve.

In some variations, the coefficient within the mathematical model characterizes a shape of the time-intensity curve. For instance, the shape of the time-intensity curve comprises a region of increasing slope of the time-intensity curve, a region of decreasing slope of the time-intensity curve, or a combination thereof. The region of increasing slope of the time-intensity curve may occur from start of measurement of the transit of the imaging agent though the vasculature of the tissue to a maximum intensity of the empirical signal intensity data, and the region of decreasing slope of the time-intensity curve may occur from a maximum intensity of the empirical signal intensity data to end of measurement of the transit of the imaging agent through the vasculature of the tissue. Furthermore, the region of increasing slope may represent an arterial phase of the curve and the region of decreasing slope may represent a venous phase of the curve.

In one particular variation, the method may utilize the mathematical model of $$f(t) = f_{Max}\left(1 - e^{-\frac{t'}{C_{Inf}}}\right)e^{-\frac{t'}{C_{Eff}}}$$

where
f(t)=signal intensity at time t
$f_{Max}$=maximum intensity;
$t'=t-t_{Lag}$;
$t_{Lag}$=influx lag time;
$C_{Inf}$=influx coefficient; and
$C_{Eff}$=efflux coefficient.

In these variations, $C_{Inf}$ represents the region of increasing slope of the time-intensity curve, and $C_{Eff}$ represents the region of decreasing slope of the time-intensity curve.

Generating the coefficient-derived image may comprise assigning a pixel intensity to each coefficient in the plurality of the coefficients, scaling the assigned pixel intensities, and or applying histogram equalization to the assigned pixel intensities. As a result, the coefficient-derived image may comprise an arterial coefficient-derived image generated from a plurality of $C_{Inf}$ coefficients, a venous coefficient-derived image generated from a plurality of $C_{Eff}$ coefficients, or a combination of the arterial coefficient-derived image and the venous coefficient-derived image.

In some variations, a heterogeneous pattern in the coefficient-derived image is indicative of an actual or suspected wound, and the method may further comprise processing the heterogeneous pattern to determine a healing status of the actual or suspected wound. In some variations, the coefficient-derived image may additionally or alternatively represent a qualitative profile of the tissue. Furthermore, the coefficient-derived image may facilitate visualization of tissue perfusion in the tissue, prognostic information of wound healing, visualization of anatomical shape of the tissue (e.g., visualization of a vessel, a vessel network, or a combination thereof).

The method may further comprise tracking a change in the coefficient-derived image over time to assess progress of healing of the tissue, efficacy of clinical intervention, or a combination thereof. For instance, the method may comprise quantifying a selected region of the coefficient-derived image to provide a quantitative indicator of the progress of healing of the tissue, efficacy of clinical intervention, or the combination thereof. Quantifying the selected region may, for example, comprise calculating of an area for the selected region, and processing the area for the selected region of a first coefficient-derived image using the area for the selected region of a second coefficient-derived image to provide the quantitative indicator. Such processing may comprise dividing the area for the selected region of the first coefficient-derived image by the area for the selected region of the second coefficient-derived image. As a result, the quantitative indicator may be indicative of an ongoing process of healing of the tissue.

In some variations, assessing the tissue of the subject comprises assessing a wound in the tissue, a peri-wound in the tissue, or a combination thereof (e.g., assessing a state of the wound, a property of the wound, a condition of the wound, a healing status of the wound, or a combination thereof, where the state of the wound, the property of the wound, the condition of the wound, or the healing status of the wound comprises inflammation, malignancy, abnormality, disease, or a combination thereof). For example, the wound may comprises an injury to the tissue, such as a surgical wound, a chronic wound, an acute wound, or a combination thereof (e.g., an incision, a pressure ulcer, a laceration, an abrasion, a puncture, a contusion, an avulsion, a cavity, a burn, a pressure ulcer, a venous ulcer, an arterial ulcer, a diabetic lower extremity ulcer, or a combination thereof).

The imaging agent may include a fluorescence imaging agent, where the empirical signal intensity data is data derived from fluorescence imaging acquired using a fluorescence imaging system. For instance, the fluorescence imaging agent may be administered to the subject immediately prior to acquisition of the empirical signal intensity data. The fluorescence imaging agent comprises a fluorescence dye, an analogue thereof, a derivative thereof, or a combination thereof. For example, the fluorescence dye may comprise a tricarbocyanine dye, such as indocyanine green (ICG). As another example, the fluorescence dye may comprise fluorescein isothiocyanate, rhodamine, phycoerythrin, phycocyanin, allophycocyanin, o-phthaldehyde, fluorescamine, rose Bengal, trypan blue, fluoro-gold, or a combination thereof.

Also disclosed herein is use of the above-described methods to discriminate between a healing wound and a non-healing wound, use of the above-described methods in clinical decision making regarding continuation of treatment, and/or use of the above-described methods in wound management, plastic surgery, reconstructive surgery, or a combination thereof. Furthermore, disclosed herein is use of the coefficient, the coefficient-derived image, or both for machine learning. Furthermore, disclosed herein is the use of the arterial coefficient-derived image and the venous coefficient-derived image for predicting a healing potential of a wound.

Generally, in another variation, there is disclosed a computer-implemented method of providing a prognosis for wound healing in tissue of a subject, the tissue comprising a wound, the method comprising: generating a time-intensity curve for a calculation region in a time series of fluorescence empirical signal intensity data obtained from the tissue, the time series of fluorescence empirical signal intensity data capturing transit of a fluorescence imaging agent through vasculature of the tissue as a function of time; processing the time-intensity curve to calculate an influx coefficient approximating an arterial portion of the time-intensity curve and an efflux coefficient approximating a venous portion of the time-intensity curve; generating an arterial coefficient-derived image of the tissue from a plurality of the influx coefficients and a venous coefficient-derived image from a plurality of the efflux coefficients, wherein the arterial coefficient-derived image comprises a first region representing the wound and the venous coefficient map comprises a second region representing the wound; and assessing the first region relative to the second region to derive an indicator of a progress of healing. In some variations, assessing the first region relative to the second region to derive the indicator of the progress of healing comprises calculating a first area for the first region and a second area for the second region; and comparing the first and second areas.

Generally, in another variations, there is disclosed a computer-implemented method operating with an imaging system, the imaging system configured to capture the transit of an imaging agent over time through the tissue wherein the system processor: utilizes a mathematical model approximating a signal intensity arising from an imaging agent circulating with blood and transiting vasculature of the tissue as a function of time to calculate a coefficient for the mathematical model at one or more points on the tissue using empirical signal intensity data for the imaging agent in the tissue, the empirical signal intensity data comprising a set of intensity values over time; and generates a coefficient-derived image of the tissue from a plurality of the coefficients, wherein a difference in the coefficients correlates with a difference in a dynamic behavior of the imaging agent in the tissue.

Generally, in another variation, there is disclosed a tangible non-transitory computer readable medium having computer-executable program code means embedded thereon comprising a method of assessing a tissue of a subject, the method comprising: providing a mathematical model approximating a signal intensity arising from an imaging agent circulating with blood and transiting vasculature of the tissue as a function of time; calculating a coefficient for the mathematical model at one or more points on the tissue using empirical signal intensity data for the imaging agent in the tissue, the empirical signal intensity data comprising a set of intensity values over time; and generating a coefficient-derived image of the tissue from a plurality of the coefficients, wherein a difference in the coefficients correlates with a difference in a dynamic behavior of the imaging agent in the tissue.

Generally, in one variation of a system for assessing a tissue of a subject, the system comprises a user interface; a processor configured to communicate with the user interface; and a non-transitory computer-readable storage medium having instructions stored. When the instructions are executed by the processor, the instructions cause the processor to perform operations including: utilizing a mathematical model approximating a signal intensity arising from an imaging agent circulating with blood and transiting vasculature of the tissue as a function of time; calculating a coefficient for the mathematical model at one or more points on the tissue using empirical signal intensity data for the imaging agent in the tissue, the empirical signal intensity data comprising a set of intensity values over time; and generating a coefficient-derived image of the tissue from a plurality of the coefficients, wherein a difference in the coefficients correlates with a difference in a dynamic behavior of the imaging agent in the tissue.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:

1. A system for allowing assessment of healing of tissue of a subject, the system comprising:
   one or more processors; and
   memory having instructions stored thereon, wherein the instructions, when executed by the one or more processors, cause the system to:
      receive a time series of signal intensity data capturing the transit of an imaging agent through tissue over a period of time, wherein the time series of signal intensity data define a plurality of calculation regions and wherein signal intensity in each calculation region over the period of time may be approximated by a time-intensity curve corresponding to that calculation region;
      determine, for each calculation region;
         a first coefficient value that is related to at least a portion of the time-intensity curve corresponding to the calculation region; and
         a second coefficient value related to at least a second portion of the time-intensity curve corresponding to the calculation region; and
         a combined coefficient value based on the first coefficient value and the second coefficient value, wherein determining the combined coefficient value based on the first coefficient value and the second coefficient value comprises weighting relative contributions of the first coefficient value and the second coefficient value;
      generate a coefficient-derived image map of perfusion in the tissue based on the combined coefficient values across the plurality of calculation regions.

2. The system of claim 1, wherein the first portion of the time intensity curve is an arterial portion of the time-intensity curve and the second portion of the time intensity curve is a venous portion of the time-intensity curve.

3. The system of claim 1, wherein:
   the first coefficient value is determined based on a first slope of a first linear regression of a first logarithmic function of intensity data of the first portion of the time intensity curve; and
   the second coefficient value is determined based on a second slope of a second linear regression of a second logarithmic function of intensity data of the second portion of the time intensity curve.

4. The system of claim 1, wherein determining the combined coefficient value based on the first coefficient value and the second coefficient value comprises deriving a differential between the first coefficient value and the second coefficient value.

5. The system of claim 1, wherein determining the combined coefficient value based on the first coefficient value and the second coefficient value comprises summing the first coefficient value and the second coefficient value.

6. The system of claim 1, wherein a heterogeneous pattern in the coefficient-derived image map is indicative of actual or suspected changes in blood flow and perfusion in the tissue.

7. A method for use in medical imaging for allowing assessment of healing of tissue of a subject, the method comprising:

at a computer system including one or more processors and memory:

receiving a time series of signal intensity data capturing the transit of an imaging agent through tissue over a period of time, wherein the time series of signal intensity data define a plurality of calculation regions and wherein signal intensity in each calculation region over the period of time may be approximated by a time-intensity curve corresponding to that calculation region;

determining, for each calculation region;
a first coefficient value that is related to at least a portion of the time-intensity curve corresponding to the calculation region; and
a second coefficient value related to at least a second portion of the time-intensity curve corresponding to the calculation region; and
a combined coefficient value based on the first coefficient value and the second coefficient value, wherein determining the combined coefficient value based on the first coefficient value and the second coefficient value comprises weighting relative contributions of the first coefficient value and the second coefficient value;

generating a coefficient-derived image map of perfusion in the tissue based on the combined coefficient values across the plurality of calculation regions.

8. The method of claim 7, wherein the first portion of the time intensity curve is an arterial portion of the time-intensity curve and the second portion of the time intensity curve is a venous portion of the time-intensity curve.

9. The method of claim 7, wherein:
the first coefficient value is determined based on a first slope of a first linear regression of a first logarithmic function of intensity data of the first portion of the time intensity curve; and
the second coefficient value is determined based on a second slope of a second linear regression of a second logarithmic function of intensity data of the second portion of the time intensity curve.

10. The method of claim 7, wherein determining the combined coefficient value based on the first coefficient value and the second coefficient value comprises deriving a differential between the first coefficient value and the second coefficient value.

11. The method of claim 7, wherein determining the combined coefficient value based on the first coefficient value and the second coefficient value comprises summing the first coefficient value and the second coefficient value.

12. The method of claim 7, wherein a heterogeneous pattern in the coefficient-derived image map is indicative of actual or suspected changes in blood flow and perfusion in the tissue.

13. A non-transitory computer-readable storage medium for use in medical imaging for allowing assessment of healing of tissue of a subject, the non-transitory computer readable storage medium storing instructions that, when executed by a computer system comprising one or more processors, cause the computer system to:

receive a time series of signal intensity data capturing the transit of an imaging agent through tissue over a period of time, wherein the time series of signal intensity data define a plurality of calculation regions and wherein signal intensity in each calculation region over the period of time may be approximated by a time-intensity curve corresponding to that calculation region;

determine, for each calculation region;
a first coefficient value that is related to at least a portion of the time-intensity curve corresponding to the calculation region; and
a second coefficient value related to at least a second portion of the time-intensity curve corresponding to the calculation region; and
a combined coefficient value based on the first coefficient value and the second coefficient value, wherein determining the combined coefficient value based on the first coefficient value and the second coefficient value comprises weighting relative contributions of the first coefficient value and the second coefficient value;

generate a coefficient-derived image map of perfusion in the tissue based on the combined coefficient values across the plurality of calculation regions.

14. The non-transitory computer-readable storage medium of claim 13, wherein the first portion of the time intensity curve is an arterial portion of the time-intensity curve and the second portion of the time intensity curve is a venous portion of the time-intensity curve.

15. The non-transitory computer-readable storage medium of claim 13, wherein:
the first coefficient value is determined based on a first slope of a first linear regression of a first logarithmic function of intensity data of the first portion of the time intensity curve; and
the second coefficient value is determined based on a second slope of a second linear regression of a second logarithmic function of intensity data of the second portion of the time intensity curve.

16. The non-transitory computer-readable storage medium of claim 13, wherein determining the combined coefficient value based on the first coefficient value and the second coefficient value comprises one or more selected from the set of:
deriving a differential between the first coefficient value and the second coefficient value; and
summing the first coefficient value and the second coefficient value.

17. The non-transitory computer-readable storage medium of claim 13, wherein a heterogeneous pattern in the coefficient-derived image map is indicative of actual or suspected changes in blood flow and perfusion in the tissue.

* * * * *